United States Patent
Genick et al.

(10) Patent No.: US 8,551,716 B2
(45) Date of Patent: Oct. 8, 2013

(54) METHODS FOR SCREENING CELLS AND ANTIBODIES

(75) Inventors: Christine C. Genick, Waltham, MA (US); Lance G. Laing, Belmont, MA (US); Peter Li, Andover, MA (US); Timothy F. Smith, Dracut, MA (US); Lara Madison, Bridgewater, MA (US); Bo Lin, Lexington, MA (US)

(73) Assignee: X-Body, Inc., Waltham, MA (US)

( * ) Notice: Subject to any disclaimer, the term of this patent is extended or adjusted under 35 U.S.C. 154(b) by 0 days.

(21) Appl. No.: 13/527,072

(22) Filed: Jun. 19, 2012

(65) Prior Publication Data

US 2013/0130926 A1 May 23, 2013

Related U.S. Application Data

(60) Division of application No. 12/758,928, filed on Apr. 13, 2010, now Pat. No. 8,202,735, which is a division of application No. 11/635,934, filed on Dec. 8, 2006, now Pat. No. 7,927,822, which is a continuation-in-part of application No. 10/667,696, filed on Sep. 22, 2003, now Pat. No. 7,264,973, which is a continuation-in-part of application No. 10/237,641, filed on Sep. 9, 2002, now Pat. No. 7,153,702, said application No. 11/635,934 is a continuation-in-part of application No. 11/490,556, filed on Jul. 20, 2006, now Pat. No. 7,863,052.

(60) Provisional application No. 60/707,579, filed on Aug. 11, 2005, provisional application No. 60/713,694, filed on Sep. 2, 2005, provisional application No. 60/778,160, filed on Feb. 28, 2006, provisional application No. 60/790,207, filed on Apr. 7, 2006.

(51) Int. Cl.
*G01N 33/53* (2006.01)

(52) U.S. Cl.
USPC ........... 435/7.2; 435/7.21; 436/164; 436/165; 436/518; 436/524; 436/525; 436/527; 436/805

(58) Field of Classification Search
None
See application file for complete search history.

(56) References Cited

U.S. PATENT DOCUMENTS

| | | | |
|---|---|---|---|
| 3,689,346 | A | 9/1972 | Rowland |
| 3,810,688 | A | 5/1974 | Ballman et al. |
| 3,856,404 | A | 12/1974 | Hershler et al. |
| 3,916,182 | A | 10/1975 | Dabby et al. |

(Continued)

FOREIGN PATENT DOCUMENTS

| | | |
|---|---|---|
| CA | 2394966 | 8/2001 |
| CA | 2395318 | 8/2001 |

(Continued)

OTHER PUBLICATIONS

Reckless and Grainger, "Identification of oligopeptide sequences which inhibit migration induced by a wide range of chemokines", Biochem. J., 340:803-811 (1999).

(Continued)

*Primary Examiner* — Chris L Chin
(74) *Attorney, Agent, or Firm* — McDonnell Boehnen Hulbert & Berghoff LLP

(57) ABSTRACT

The invention provides methods of detecting a change in cell growth patterns, methods of screening many different antibodies in one receptacle, and methods of detecting specific binding of an antibody to a protein or cell, wherein the antibody is in a mixture of many different antibodies.

16 Claims, 20 Drawing Sheets

CELL CAPTURE ON THE BIND BIOSENSOR™ VIA AN IMMOBILIZED

(56) References Cited

U.S. PATENT DOCUMENTS

| | | | |
|---|---|---|---|
| 4,009,933 A | 3/1977 | Firester |
| 4,050,895 A | 9/1977 | Hardy et al. |
| 4,240,751 A | 12/1980 | Linnecke et al. |
| 4,289,371 A | 9/1981 | Kramer |
| 4,344,438 A | 8/1982 | Schultz |
| 4,420,502 A | 12/1983 | Conley |
| 4,536,608 A | 8/1985 | Sheng et al. |
| 4,560,248 A | 12/1985 | Cramp et al. |
| 4,576,850 A | 3/1986 | Martens |
| 4,608,344 A | 8/1986 | Carter et al. |
| 4,650,329 A | 3/1987 | Barrett et al. |
| 4,652,290 A | 3/1987 | Cho et al. |
| 4,668,558 A | 5/1987 | Barber |
| 4,701,008 A | 10/1987 | Richard et al. |
| 4,810,658 A | 3/1989 | Shanks et al. |
| 4,815,843 A | 3/1989 | Tiefenthaler et al. |
| 4,818,710 A | 4/1989 | Sutherland et al. |
| 4,857,273 A | 8/1989 | Stewart et al. |
| RE33,064 E | 9/1989 | Carter |
| 4,876,208 A | 10/1989 | Gustafson et al. |
| 4,882,288 A | 11/1989 | North et al. |
| 4,888,260 A | 12/1989 | Cowan |
| 4,931,384 A | 6/1990 | Layton et al. |
| 4,952,056 A | 8/1990 | Tiefenthaler |
| 4,958,895 A | 9/1990 | Wells et al. |
| 4,992,385 A | 2/1991 | Godfrey |
| 4,999,234 A | 3/1991 | Cowen |
| 4,999,484 A | 3/1991 | Kaneko |
| 5,071,248 A | 12/1991 | Tiefenthaler et al. |
| 5,118,608 A | 6/1992 | Layton et al. |
| 5,155,785 A | 10/1992 | Holland et al. |
| 5,156,785 A | 10/1992 | Zdrahala |
| 5,170,448 A | 12/1992 | Ackley et al. |
| 5,175,030 A | 12/1992 | Lu et al. |
| 5,210,404 A | 5/1993 | Cush et al. |
| 5,216,680 A | 6/1993 | Magnusson et al. |
| 5,229,614 A | 7/1993 | Andersson et al. |
| 5,242,828 A | 9/1993 | Bergstrom et al. |
| 5,268,782 A | 12/1993 | Wenz et al. |
| 5,310,686 A | 5/1994 | Sawyers et al. |
| 5,337,183 A | 8/1994 | Rosenblatt |
| 5,413,884 A | 5/1995 | Koch et al. |
| 5,442,169 A | 8/1995 | Kunz |
| 5,455,178 A | 10/1995 | Fattinger |
| 5,475,780 A | 12/1995 | Mizrahi |
| 5,478,527 A | 12/1995 | Gustafson et al. |
| 5,478,756 A | 12/1995 | Gizeli et al. |
| 5,492,840 A | 2/1996 | Malmquist et al. |
| 5,496,701 A | 3/1996 | Pollard-Knight |
| 5,559,338 A | 9/1996 | Elliott et al. |
| 5,598,267 A | 1/1997 | Sambles et al. |
| 5,598,300 A | 1/1997 | Magnusson et al. |
| 5,601,997 A | 2/1997 | Tchao |
| 5,606,170 A | 2/1997 | Saaski et al. |
| 5,615,052 A | 3/1997 | Doggett |
| 5,629,214 A | 5/1997 | Crosby |
| 5,631,171 A | 5/1997 | Sandstrom et al. |
| 5,666,197 A | 9/1997 | Guerra |
| 5,690,894 A | 11/1997 | Pinkel et al. |
| 5,691,846 A | 11/1997 | Benson et al. |
| 5,732,173 A | 3/1998 | Bylander et al. |
| 5,738,825 A | 4/1998 | Rudigier et al. |
| 5,768,461 A | 6/1998 | Svetkoff et al. |
| 5,771,328 A | 6/1998 | Wortman et al. |
| 5,792,411 A | 8/1998 | Morris et al. |
| 5,801,390 A | 9/1998 | Shiraishi |
| 5,804,453 A | 9/1998 | Chen |
| 5,814,516 A | 9/1998 | Vo-Dinh |
| 5,814,524 A | 9/1998 | Walt et al. |
| 5,821,343 A | 10/1998 | Keogh |
| 5,864,641 A | 1/1999 | Murphy et al. |
| 5,922,550 A | 7/1999 | Everhart et al. |
| 5,925,878 A | 7/1999 | Challener |
| 5,955,335 A | 9/1999 | Thust et al. |
| 5,955,378 A | 9/1999 | Challener |
| 5,955,729 A | 9/1999 | Nelson |
| 5,986,762 A | 11/1999 | Challener |
| 5,991,480 A | 11/1999 | Kunz et al. |
| 5,994,150 A | 11/1999 | Challener et al. |
| 5,998,298 A | 12/1999 | Hetherington et al. |
| 6,035,089 A | 3/2000 | Grann et al. |
| 6,042,998 A | 3/2000 | Brueck et al. |
| 6,052,213 A | 4/2000 | Burt et al. |
| 6,076,248 A | 6/2000 | Hoopman et al. |
| 6,088,505 A | 7/2000 | Hobbs |
| 6,100,991 A | 8/2000 | Challener |
| 6,128,431 A | 10/2000 | Siminovitch |
| 6,146,593 A | 11/2000 | Pinkel et al. |
| 6,174,677 B1 | 1/2001 | Vo-Dinh |
| 6,185,019 B1 | 2/2001 | Hobbs et al. |
| 6,200,737 B1 | 3/2001 | Walt et al. |
| 6,215,928 B1 | 4/2001 | Friesem et al. |
| 6,218,194 B1 | 4/2001 | Lyndin et al. |
| 6,235,488 B1 | 5/2001 | Tom-Moy et al. |
| 6,277,653 B1 | 8/2001 | Challener |
| 6,303,179 B1 | 10/2001 | Koulik et al. |
| 6,316,153 B1 | 11/2001 | Goodman et al. |
| 6,320,991 B1 | 11/2001 | Challener et al. |
| RE37,473 E | 12/2001 | Challener |
| 6,332,663 B1 | 12/2001 | Puzio et al. |
| 6,338,968 B1 | 1/2002 | Hefti |
| 6,340,598 B1 | 1/2002 | Herron et al. |
| 6,346,376 B1 | 2/2002 | Sigrist et al. |
| 6,377,721 B1 | 4/2002 | Walt et al. |
| 6,395,558 B1 | 5/2002 | Duveneck et al. |
| 6,404,554 B1 | 6/2002 | Lee et al. |
| 6,449,097 B1 | 9/2002 | Zhu et al. |
| 6,558,957 B1 | 5/2003 | Roinestad et al. |
| 6,570,657 B1 | 5/2003 | Hoppe et al. |
| 6,579,673 B2 | 6/2003 | McGrath et al. |
| 6,587,276 B2 | 7/2003 | Daniell |
| 6,661,952 B2 | 12/2003 | Simpson et al. |
| 6,707,561 B1 | 3/2004 | Budach et al. |
| 6,748,138 B2 | 6/2004 | Wang et al. |
| 6,771,376 B2 | 8/2004 | Budach et al. |
| 6,867,869 B2 | 3/2005 | Budach et al. |
| 6,870,624 B2 | 3/2005 | Hobbs et al. |
| 6,870,630 B2 | 3/2005 | Budach et al. |
| 6,902,703 B2 | 6/2005 | Marquiss et al. |
| 6,951,715 B2 | 10/2005 | Cunningham |
| 6,982,171 B2 | 1/2006 | Kim |
| 6,990,259 B2 | 1/2006 | Cunningham |
| 7,018,838 B2 | 3/2006 | Murphy |
| 7,023,544 B2 | 4/2006 | Cunningham |
| 7,033,819 B2 | 4/2006 | Kim |
| 7,033,821 B2 | 4/2006 | Kim |
| 7,064,844 B2 | 6/2006 | Budach et al. |
| 7,070,987 B2 | 7/2006 | Cunningham |
| 7,074,311 B1 | 7/2006 | Cunningham |
| 7,094,595 B2 | 8/2006 | Cunningham |
| 7,101,660 B2 | 9/2006 | Cunningham et al. |
| 7,118,710 B2 | 10/2006 | Cunningham |
| 7,142,296 B2 | 11/2006 | Cunningham et al. |
| 7,148,964 B2 | 12/2006 | Cunningham et al. |
| 7,153,702 B2 | 12/2006 | Lin |
| 7,158,230 B2 | 1/2007 | Cunningham et al. |
| 7,162,125 B1 | 1/2007 | Schulz |
| 7,170,599 B2 | 1/2007 | Cunningham et al. |
| 7,175,980 B2 | 2/2007 | Qiu et al. |
| 7,197,198 B2 | 3/2007 | Schulz et al. |
| 7,202,076 B2 | 4/2007 | Cunningham et al. |
| 7,217,574 B2 | 5/2007 | Pien et al. |
| 7,264,973 B2 | 9/2007 | Lin et al. |
| 7,267,993 B2 | 9/2007 | Pentreko |
| 7,292,336 B2 | 11/2007 | Cunningham et al. |
| 7,298,477 B1 | 11/2007 | Cunningham et al. |
| 7,300,803 B2 | 11/2007 | Lin et al. |
| 7,301,628 B2 | 11/2007 | Cunningham et al. |
| 7,306,827 B2 | 12/2007 | Li et al. |
| 7,309,614 B1 | 12/2007 | Baird |
| 7,312,090 B2 | 12/2007 | Lin et al. |
| 7,327,454 B2 | 2/2008 | Cunningham et al. |
| 7,396,675 B2 | 7/2008 | Pawlak et al. |
| 7,400,399 B2 | 7/2008 | Wawro et al. |

| | | |
|---|---|---|
| 7,479,404 B2 | 1/2009 | Cunningham |
| 7,483,127 B1 | 1/2009 | Li |
| 7,497,992 B2 | 3/2009 | Cunningham |
| 7,521,769 B2 | 4/2009 | Cunningham |
| 7,524,625 B2 | 4/2009 | Madison |
| 7,534,578 B1 | 5/2009 | Baird |
| 7,620,276 B2 | 11/2009 | Schulz |
| 7,628,085 B2 | 12/2009 | Laing |
| 7,742,662 B2 | 6/2010 | Cunningham |
| 7,756,365 B2 | 7/2010 | Cunningham |
| 7,790,406 B2 | 9/2010 | Cunningham |
| 2002/0018610 A1 | 2/2002 | Challener et al. |
| 2002/0028045 A1 | 3/2002 | Yoshimura |
| 2002/0028480 A1 | 3/2002 | Maher |
| 2002/0076747 A1 | 6/2002 | Price |
| 2002/0123050 A1 | 9/2002 | Poponin |
| 2002/0127565 A1 | 9/2002 | Cunningham et al. |
| 2002/0135752 A1 | 9/2002 | Sokolov et al. |
| 2002/0171045 A1 | 11/2002 | Perraut |
| 2003/0003599 A1 | 1/2003 | Wagner et al. |
| 2003/0017580 A1 | 1/2003 | Cunningham |
| 2003/0017581 A1 | 1/2003 | Li |
| 2003/0026891 A1 | 2/2003 | Qiu |
| 2003/0027327 A1 | 2/2003 | Cunningham et al. |
| 2003/0027328 A1 | 2/2003 | Cunningham et al. |
| 2003/0032039 A1 | 2/2003 | Cunningham |
| 2003/0059855 A1 | 3/2003 | Cunningham |
| 2003/0068657 A1 | 4/2003 | Lin |
| 2003/0077660 A1 | 4/2003 | Pien |
| 2003/0092075 A1 | 5/2003 | Pepper |
| 2003/0104479 A1 | 6/2003 | Bright |
| 2003/0108954 A1 | 6/2003 | Mutz |
| 2003/0113766 A1 | 6/2003 | Pepper |
| 2003/0148542 A1 | 8/2003 | Pawlak |
| 2003/0210396 A1 | 11/2003 | Hobbs et al. |
| 2003/0224369 A1 | 12/2003 | Surber et al. |
| 2004/0005540 A1 | 1/2004 | Pentreko |
| 2004/0011965 A1 | 1/2004 | Hodgkinson |
| 2004/0091397 A1 | 5/2004 | Picard |
| 2004/0132172 A1 | 7/2004 | Cunningham |
| 2004/0132214 A1 | 7/2004 | Lin |
| 2004/0151626 A1 | 8/2004 | Cunningham |
| 2004/0191757 A1 | 9/2004 | Maher |
| 2004/0219619 A1 | 11/2004 | Fernandez-Salas |
| 2005/0058639 A1 | 3/2005 | Gudas |
| 2005/0074825 A1 | 4/2005 | Luo |
| 2005/0214803 A1 | 9/2005 | Wang |
| 2005/0221271 A1 | 10/2005 | Murphy |
| 2005/0227374 A1 | 10/2005 | Cunningham et al. |
| 2006/0003372 A1 | 1/2006 | Li |
| 2006/0030033 A1 | 2/2006 | Cunningham |
| 2006/0040376 A1 | 2/2006 | Cunningham et al. |
| 2006/0057707 A1 | 3/2006 | Lin et al. |
| 2006/0181705 A1 | 8/2006 | Cunningham et al. |
| 2006/0193550 A1 | 8/2006 | Wawro et al. |
| 2006/0275825 A1 | 12/2006 | Baird |
| 2006/0281077 A1 | 12/2006 | Lin |
| 2006/0286663 A1 | 12/2006 | Cunningham et al. |
| 2007/0015210 A1 | 1/2007 | Ezekiel |
| 2007/0041012 A1 | 2/2007 | Cunningham et al. |
| 2007/0054339 A1 | 3/2007 | Lin |
| 2007/0070355 A1 | 3/2007 | Cunningham et al. |
| 2007/0141231 A1 | 6/2007 | Cunningham et al. |
| 2007/0172894 A1 | 7/2007 | Genick et al. |
| 2007/0299029 A1 | 12/2007 | Zhuo |
| 2008/0213910 A1 | 9/2008 | Jogikalmath |
| 2008/0219892 A1 | 9/2008 | Cunningham |
| 2008/0240543 A1 | 10/2008 | Budach |
| 2008/0299673 A1 | 12/2008 | Wagner |
| 2009/0130703 A1 | 5/2009 | Wagner |
| 2009/0137422 A1 | 5/2009 | Laing |
| 2009/0148955 A1 | 6/2009 | Cunningham |
| 2009/0176658 A1 | 7/2009 | Madison |
| 2009/0179637 A1 | 7/2009 | Cunningham |
| 2009/0192049 A1 | 7/2009 | Baird |
| 2009/0227469 A1 | 9/2009 | Conklin |
| 2009/0264314 A1 | 10/2009 | Cunningham |
| 2009/0269244 A1 | 10/2009 | Cunningham |
| 2009/0282931 A1 | 11/2009 | Laing |
| 2009/0305304 A1 | 12/2009 | Laing |
| 2010/0003743 A1 | 1/2010 | Schulz |
| 2010/0008826 A1 | 1/2010 | Schulz |
| 2010/0015721 A1 | 1/2010 | Laing |
| 2010/0043571 A1 | 2/2010 | Laing |
| 2010/0143959 A1 | 6/2010 | Cunningham |
| 2010/0195099 A1 | 8/2010 | Rockney |
| 2010/0196925 A1 | 8/2010 | Genick |
| 2010/0202923 A1 | 8/2010 | Cunningham |
| 2010/0227769 A1 | 9/2010 | Schulz |
| 2010/0231907 A1 | 9/2010 | Pien |
| 2010/0291575 A1 | 11/2010 | Shamah |

FOREIGN PATENT DOCUMENTS

| | | |
|---|---|---|
| CH | 669050 | 2/1989 |
| CH | 670521 | 6/1989 |
| EP | 0075353 | 3/1983 |
| EP | 0112721 | 7/1984 |
| EP | 0326219 | 1/1989 |
| EP | 0517777 | 5/1996 |
| EP | 0660924 | 9/1999 |
| EP | 1031828 | 8/2000 |
| EP | 1085315 | 3/2001 |
| FR | 2801977 | 12/1999 |
| GB | 2156970 | 10/1985 |
| GB | 2227089 | 7/1990 |
| JP | 1993228946 | 9/1993 |
| WO | 81/00912 | 2/1981 |
| WO | 84/02578 | 7/1984 |
| WO | 86/07149 | 12/1986 |
| WO | 90/08313 | 7/1990 |
| WO | 91/13339 | 9/1991 |
| WO | 92/04653 | 3/1992 |
| WO | 92/21768 | 12/1992 |
| WO | 93/17392 | 7/1993 |
| WO | 95/03538 | 2/1995 |
| WO | 96/38726 | 5/1996 |
| WO | 97/29362 | 8/1997 |
| WO | 98/10288 | 3/1998 |
| WO | 98/57200 | 12/1998 |
| WO | 99/09369 | 2/1999 |
| WO | 99/09392 | 2/1999 |
| WO | 99/54714 | 10/1999 |
| WO | 99/66330 | 12/1999 |
| WO | 00/23793 | 4/2000 |
| WO | 00/29830 | 5/2000 |
| WO | 01/02839 | 1/2001 |
| WO | 01/04697 | 1/2001 |
| WO | 01/79559 | 10/2001 |
| WO | 01/92870 | 12/2001 |
| WO | 02/061429 | 8/2002 |
| WO | 03/074548 | 9/2003 |
| WO | 2007/064702 | 6/2007 |
| WO | 2009/009718 | 1/2009 |
| WO | 2010005600 | 1/2010 |
| WO | 2010/075033 | 7/2010 |

OTHER PUBLICATIONS

Jackson, et al., "Pharmacologic Actions of the Second-Generation Leukotriene B4 Receptor Antagonist LY293111: In Vitro Studies", The Journal of Pharmacology and Experimental Therapeutics, vol. 288, No. 1, 288:286-294 (1999).

Taguchi et al., "Patterns for RANTES Secretion and Intercellular Adhesion Molecule 1 Expression Mediate Transepithelial T Cell Traffic Based on Analyses In Vitro and In Vivo", J. Exp. Med., vol. 187, No. 12, p. 1927-1940 (1998).

Dharmawardhane et al., "Localization of p21-Activated Kinase 1 (PAK1) to Pinocytic Vesicles and Cortical Actin Structures in Stimulated Cells", The Journal of Cell Biology, vol. 138, No. 6, p. 1265-1278 (1997).

Calderwood, "Integrin activation", Journal of Cell Science, 117:657-666 (2004).

Fleming et al., "PDE4-regulated cAMP degradation controls the assembly of integrin-dependent actin adhesion structures and REF52 cell migration", Journal of Cell Science, 117:2377-2388 (2004).

Mammoto et al., "Role of RhoA, mDia and ROCK in cell Shape-dependent Control of the Skp2-p27(kip1) Pathway and the G1/S Transition", The Journal of Biological Chemistry, 279:26323-26330 (2004).

Desire et al., "RAC1 Inhibition Targets Amyloid Precursor Protein Processing by y-Secretase and Decreases AB Production in Vitro and in Vivo", The Journal of Biological Chemistry, vol. 280, No. 45, p. 37516-37525 (2005).

Kim et al., "Chemokines: signal lamps for trafficking of T and B cells for development and effector function", Journal of Leukocyte Biology, 65:6-15 (1999).

Montresor et al., "Comparative Analysis of Normal versus CLL B-Lymphocytes Reveals Patient-Specific Variability in Signaling Mechanisms Controlling LFA-1 Activation by Chemokines", Cancer Res. 69(24):9281-9290 (2009).

Pelish et al., "Secramine inhibits Cdc42-deopendent functions in cells and Cdc42 activation in vitro", Nature Chemical Biology, 2:39-46 (2006).

Buckley et al., "Cel adhesion: more than just glue (Review)", Molecular Membrane Biology, 15:167-176 (1998).

Brecht et al., "Optical probes and transducers", Biosensors & Bioelectronics, vol. 10, pp. 923-936 (1995).

Challener et al., "A multilayer grating-based evanescent wave sensing technique", Sensors and Actuators B, 71, pp. 42-46 (2000).

Cowan, "Aztec surface-relief volume diffractive structure", J. Opt. Soc. Am. vol. 7, No. 8, pp. 1529-1544 (1990).

Cowan, "Holographic honeycomb microlens", Optical Engineering, vol. 24, No. 5, pp. 796-802 (1985).

Cowan, "The Recording and Large Scale Replication of Crossed Holographic Grating Arrays using Multiple Beam Interferometry", SPIE, vol. 503, Application, Theory, and Fabrication of Periodic Structures, pp. 120-129 (1984).

Cowan et al., "The Recording and Replication of Holographic Micropatterns for the Ordering of Photographic Emulsion Grains in Film Systems", J. Imaging Sci., vol. 31, No. 3, pp. 100-107 (1987).

Introduction to Bioanalytical Sensors (Techniques in Analytical Chemistry) (Cunningham ed., 1988) pp. 260-291, "Optical Based Energy Transduction", Wiley Interscience, Hoboken, NJ.

Hobbs et al., "Automated Interference Lithography Systems for Genereation of Sub-Micron Feature Size Patterns", SPIE, vol. 3879, pp. 124-135 (1999).

Huber et al., "Direct optical immunosensing (sensitivity and selectivity)", Sensors and Actuators B, 6, pp. 122-126 (1992).

Jenison et al., "Interference-based detection of nucleic acid targets on optically coated silicon", Nature Biotechnology, vol. 19, pp. 62-64 (2001).

Jin et al., "A biosensor concept based on imaging ellipsometry for visualization of biomolecular interactions", Analytical Biochemistry, vol. 232, pp. 69-72 (1995).

Jordan et al., "Surface Plasmon Resonance Imaging Measurements of Electrostatic Biopolymer Adsorption onto Chemically Modified Gold Surfaces", Analytical Chemistry, vol. 69, No. 7, pp. 1449-1456 (1997).

Lin et al., A Porous Silicon-Based Optical Interferometric Biosensor:, Science, vol. 278, pp. 840-843 (1997).

Magnusson et al., "New principle for optical filters", Appl. Phys. Lett., vol. 61, No. 9, pp. 1022-1024 (1992).

Magnusson et al., "Transmission bandpass guided-mode resonance filters", Applied. Optics, vol. 34, No. 35, pp. 8106-8109 (1995).

Morhard et al., "Immobilization of antibodies in micropatterns for cell detection by optical diffraction", Sensors and Actuators B, 70, pp. 232-242 (2000).

Pandey et al, "Proteomics to study genes and genomes", Natures 405(6788):837-46 (2000).

Patel et al., "Electrically tuned and polarization insensitive Fabry-Perot etalon with a liquid-crysatl film", App. Phys. Lett., vol. 58, No. 22, pp. 2491-2493 (1993).

Bertoni et al., "Frequency-Selective Reflection and Transmission by a Periodic Dielectric Layer", IEEE Transaction on Antennas and Propagation, vol. 37, No. 1, pp. 78-83 (1989).

Brundrett et al., "Normal-incidence guided-mode resonant grating filters: design and experimental demonstration", Optics Letters, vol. 23, No. 9, pp. 700-702 (1998).

Peng "Polarization-control Components and Narrow-band Filters Based on Subwavelength Grating Structures", 1996.

Statement of Applicants dated May 10, 2004.

Leanu, Torben, Material, Silicon Nitride, 1996, 97, 98.

Cerac, Technical publications: Tantalum Oxide, Ta2O5 for Optical Coating, 2000, Cerac, Inc.

Neuschafer et al., Evanescent resonator chips: a universal platform with superior sensitivity for fluorescence-based microarrays, Biosensors & Bioelectronics, 18, pp. 489-497 (2003).

Budach et al., "Generation of transducers for fluorescence-based microarrays with enhanced sensitivity and their application for gene expression profiling", Analytical Chemistry, 1;75(11):2571-7 (2003).

Anderson et al., "Proteomics: applications in basic and applied biology", Current Opinion in Biotechnology, 11:408-412 (2000).

MacBeath et al., "Printing Proteins as Microarrays for High-Throughput Function Determination", Science, vol. 289, pp. 1760-1763 (2000).

deWildt et al, "Antibody arrays for high-throughput screening of antibody-antigen interactions", Nature Biotechnology, vol. 18, pp. 989-994 (2000).

Cunningham et al., "A plastic colorimetric resonant optical biosensor for multiparallel detection of label-free biochemical interactions" Sensors and Actuators B, 85, pp. 219-226 (2002).

Caruso et al., "Quartz Crystal Microbalance Study of DNA Immobilization and Hybridization for Nucleic Acid Sensor Development", Analytical Chemistry, vol. 69, No. 11, pp. 2043-2049 (1997).

Hefti et al., "Sensitive detection method of dielectric dispersions in aqueous-based, surface-bound macromolecular structures using microwave spectroscopy", Applied Physics Letters, vol. 75, No. 12, pp. 1802-1084 (1999).

Wu et al., "Bioassay of prostate-specific antigen (PSA) using microcantilevers", Nature Biotechnology, vol. 19, pp. 856-860 (2001).

Wasserman et al., "Structure and Reactivity of Alkylsiloxane Monolayers Formed by Reaction of Alkyltrichlorosilanes on Silicone Substrates", Langmuir, 5, pp. 1074-1087 (1989).

Kallury et al., "X-ray Photoelectron Spectroscopy of Silica Surfaces Treated with Polyfunctional Silanes", Anal. Chem. 60, 169-172 (1988).

Cunningham et al., "Colorimetric resonant reflection as a direct biochemical assay technique", Sensors and Actuators B, 81 (2002) 316-328.

Mullaney et al, "Epitope Mapping of Neutralizing Botulinum Neurotoxin A Antibodies by Phage Display", Infection and Immunity, vol. 69, No. 10, pp. 6511-6514 (2001).

Nellen et al., "Integrated Optical Input Grating Couplers as Biochemical Sensors", Sensors and Actuators, 15 (1988) 285-295.

Lukosz and Tiefenthaler, "Embossing technique for fabricating integrated optical components in hard inorganic waveguiding materials", Optics Letters vol. 8, pp. 537-539 (1983).

Tiefenthaler and Lukosz, "Integrated optical switches and gas sensors", Optics Letters, vol. 10, pp. 137-139 (1984).

Chabay, "Optical Waveguides", Analytical Chemistry, vol. 54, pp. 1071A-1081A (1982).

Sutherland et al., "Optical Detection of Antibody-antigen Reactions at a Glass-Liquid Interface", Clin. Chem. vol. 30, pp. 1533-1538 (1984).

Holm and Palik, "Internal-reflection spectroscopy", Laser Focus, vol. 15, pp. 60-65 (1979).

Harrick and Loeb, "Multiple Internal Reflection Fluorescence Spectrometry", Analytical Chemistry, vol. 45, pp. 687-691 (1973).

Tien, "Light Waves in This Films and Integrated Optics", Applied Optics, vol. 10, pp. 2395-2413 (1971).

Dakss et al., "Grating Coupler for Efficient Excitation of Optical Guided Waves in Thin Films", Applied Physics Letters, vol. 16, pp. 523-525 (1970).

Sutherland et al., "Immunoassays at a Quartz-Liquid Interface: Theory, Instrumentation and Preliminary Application to Fluorescent Immunoassay of Human Immunoglobulin G", Journal of Immunological Methods, vol. 74, pp. 253-265 (1984).

English Translation of CH 670 521 A5 (Jun. 15, 1989), translation dated Oct. 28, 2003.

English Translation of CH 669 050 A5 (Feb. 15, 1989), translation dated Oct. 29, 2003.
Patel et al., "Multi-Wavelength Tunable Liquid-Crystal Etalon Filter", IEEE Photonics Technology Letters, vol. 3, No. 7, pp. 643-644 (1991).
Takeda et al., "The Integrins", Genome Biology, 8:215 (2007).
Sancho et al., "Binding kinetics of monomeric and aggregated IgG to Kupffer cells and hepatocytes of mice", Immunology, 53:283 (1984).
Chaplen et al., "Improvement of Bioactive Compound Classification through Integration of Orthogonal Cell-Based Biosensing Methods", Sensors, 7:38-51(2007).
U.S. Appl. No. 13/166,936, filed Jun. 23, 2011.
U.S. Appl. No. 13/073,233, filed Mar. 28, 2011.
English Translation of CH 670 521 A5 (Jun. 15, 1989), translation dated Oct. 29, 2003.
Patterson, "Proteomics: the Industrialization of protein chemistry", Current Opinions in Biotechnology, 11(4):413-8 (2000).
Peng et al., "Experimental demonstration of resonant anomalies in diffraction from two-dimensional gratings", Optics Letters, vol. 21, No. 8, pp. 549-551 (1996).
Peng et al., "Resonant scattering from two-dimensional gratings", J. Opt. Soc. Am. A., vol. 13, No. 5, pp. 993-1005 (1996).
Raguin et al., "Structured Surfaces Mimic Coating Performance", Laser Focus World, pp. 113-117 (1997).
Sigal et al., "A Self-Assembled Monolayer for the Binding and Study of Histidine-Tagged Proteins by Surface Plasmon Resonance", Analytical Chemistry, vol. 68, No. 3, pp. 490-497 (1996).
Wang et al., "Design of waveguide-grating filters with symmetrical line shapes and low sidebands", Optical Society of America, vol. 19, No. 12, pp. 919-921 (1994).
Wang et al., "Guided-mode resonances in planar dielectric-layer diffraction gratings", J. Opt. Soc. Am., vol. 7, No. 8, pp. 1470-1474 (1990).
Wang et al., "Theory and applications of guided-mode resonance filter", Applied Optics, vol. 32, No. 14, pp. 2606-2613 (1993).
International Search Report for application PCT/US01/50723, Sep. 17, 2002.
International Search Report for application PCT/US03/01175, Aug. 18, 2003.
Invitation to Pay Additional Fees in application PCT/US01/50723, Aug. 30, 2002.
Haidner, "Zero-Order Gratings Used as an Artificial Distributed Index Medium", Optik, Wissenschaftliche Verlag GmbH, Stuttgart, DE, vol. 89, No. 3, pp. 107-112 (1992).
Wilson et al., "The Optical Properties 1-19 of 'Moth Eye' Antireflection Surfaces", Optica Acta, vol. 29, No. 7, pp. 993-1009 (1982).
Bagnich et al., "Tunable Optical Filter", Derwent Publications, English Translation, Abstract Only,Derwent Publications Ltd. (Mar. 15, 1989).
*Corning Inc.* v. *SRU Biosystems, Inc.*, Memorandum Opinion dated Nov. 15, 2005 in the United States District Court for the district of Delaware.
Liu et al., "Development of an optical fiber lactate sensor", Mikrochimica Acta, 131(1-2), pp. 129-135 (1999).
Magnusson et al., "Fiber Endface Bioprobes with high Sensitivity and Spatial Resolution", Grant Proposal dated Aug. 11, 1999.
Norton, "Resonant Grating Structures: Theory, Design and Applications", Doctoral Thesis, The University of Rochester, 1997.
Popov et al., "Theoretical study of the anomalies of coated dielectric gratings", Optica Acta, vol. 33, No. 5, pp. 607-619 (1986).
Shin et al., "Thin-film optical filters with diffractive elements and waveguides", Opt. Eng. 37(9):2634-2646 (1998).
Tibuleac et al., "Reflection and transmission guided-mode resonance filters", J. Opt. Soc. Am. A., vol. 14, No. 7, pp. 1617-1626 (1997).
Tibuleac et al., "Diffractive Narrow-Band Transmission Filters Based on Guided-Mode Resonance Effects in Thin-Film Multilayers", IEEE Photonics Technology Letters, vol. 9, No. 4, pp. 464-466 (1997).
Wawro, "Design, Fabrication and Testing of Waveguide Gratings for Spectral Filters, Photonic Antennas and Optical Fiber Sensors", Presentation, University of Texas at Arlington (1999).
Wawro et al., "Novel diffractive structures integrating waveguide-gratings on optical fiber endfaces", Presentation, Graduate Student Research Symposium (1999).
Tibuleac, "Guided-mode resonance reflection and transmission filters in the optical and microwave spectral ranges", Doctoral Dissertation Defense (1999).
Yariv, "Coupled-Mode Theory for Guided-Wave Optics", IEEE Journal of Quantum Electronics, vol. 9, No. 9, p. 919-933 (1973).
Wang et al., "Resonance of Asymmetric Dielectric Waveguides Containing a Diffraction Grating", IEEE (1990).
Hessel et al., "A New Theory of Wood's Anomalies on Optical Gratings", Applied Optics, vol. 4, No. 10, p. 1275-1299 (1965).
Lukosz et al., "Sensitivity of Integrated Optical Grating and Prism Couplers as (Bio)chemical Sensors", Sensors and Actuators, 15, p. 273-284 (1988).
Neviere et al., "About the Theory of Optical Grating Coupler-Waveguide Systems", Optics Communications, vol. 8, No. 2, p. 113-117 (1973).
Gaylord et al., "Analysis and Applications of Optical Diffraction by Gratings", IEEE, 73(5):894, p. 894-924 (1985).
Chaplen et al., "Improvement of Bioactive Compound Classification through Integration of Orthogonal Cell-Based Biosensing Methods", Sensors, 7:38-51 (2007).
Wawro et al., "Optical fiber endface biosensor based on resonances in dielectric waveguide gratings", Biomedical Diagnostic Guidance and Surgical-Assist Systems II, Vo-Dihn et al. eds., Proceedings of SPIE, 3911:86-94 (2000).
Office action dated Apr. 2, 2007, for U.S. Appl. No. 11/506,639 (now U.S. Patent No. 7,298,477).
International Search Report for foreign counterpart application PCT/US01/50723, Sep. 17, 2002.
International Search Report for foreign counterpart application PCT/US03/01175, Aug. 18, 2003.
Invitation to Pay Additional Fees in foreign counterpart application PCT/US01/50723, Aug. 30, 2002.
U.S. Appl. No. 11/635,934, filed Dec. 8, 2006.
U.S. Appl. No. 11/566,818, filed Dec. 5, 2006.
U.S. Appl. No. 11/506,639, filed Aug. 18, 2007.
U.S. Appl. No. 11/749,079, filed May 15, 2007.
U.S. Appl. No. 11/828,076, filed Jul. 25, 2007.
European Search Report for EP 07 11 8355 dated Feb. 5, 2008.
Nelson, et al., "BIA/MS of Epitope-Tagged Peptides Directly from *E. coli* Lysate: Multiplex Detection and Protein Identification at Low-Femtomole to Subfemtomole Levels", Anal. Chem. 1999, 71, 2858-2865.
Moffatt, "Optical probes May Hasten Shift of Diagnostics from Lab to Doc's Office", Genetic Engineering News, vol. 18, (1986), p. 18.
Williams, et al., "The integration of SPR biosensors with mass spectrometry: possible applications for proteome analysis", Trends in Microbiology, Elsevier, vol. 18, No. 2 (2000) pp. 45-48.
Cekaite et al., "Analysis of the humoral immune response to immunoselected phage-displayed peptides by a microarray-based method", Proteomics 2004, 4, 2572-2582.
Sun et al., "Use of bioluminescent *Salmonella* for assessing the efficiency of constructed phage-based biosorbent", Journal of Industrial Microbiology & Biotechnology, 2000, 25, 273-275.
Wan, et al., "Landscape phage-based magnetostrictive biosensor for detecting *Bacillus anthracis* spores", Proc. IEEE Sens., 2005, 1308-1311.
Cunningham, et al., "Label-Free Assays on the Bind System", Journal of Biomolecular Screening, vol. 9, p. 481-490 (2004).
Cunningham, "Label-Free Detection with the Bind System", Presented at Screentech General, Mar. 24, 2003.
Baird, "Beyond Elisa's: Label-free Detectionw ith Bind", Presented at Interphex Meeting in Europe, Mar. 16-18, 2004.
Cunningham, et al., "Colorimetric Resonant Reflection as a Direct Biochemical Assay Technique", Presented at the Pittsburgh Conference and Exposition on Analytical Chemistry and Applied Spectroscopy, Morial Convention Center in New Orleans, LA Mar. 17-22, 2002.
Broad et al., "Growth and adipose differentiation of sheep preadipocyte fibroblasts in serum-free medium", Eur. J. Biochem., 135, 33-39 (1983).

Castillo et al., "Characterization of proliferation and differentiation of EGF-response striatal and septal precursor cells", Int. J. Devl. Neuroscience 21 (2003) 41-47.

Chalazonitis, et al., "The a1 Subunit of Laminin-1 Promotes the Development of Neurons by Interacting with LBP110 Expressed by Neural Crest-Derived Cells Immunoselected from the Fetal Mouse Gut", J. Neurobiol. 33:118-138, 1997.

Hao et al., "Fetal Human Hemotopoietic Stem Cells Can Differentiate Sequentially into Neural Stem Cells and then Astrocytes in Vitro", Journal of Hematotherapy & Stem Cell Research, 12:23-32 (2003).

Kano, et al., "Establishment of Hepatic Stem-like Cell Lines from Normal Adult Porcine Liver in a Poly-D-Lysine-Coated Dish with Nair-1 Medium", In Vitro Cell. Dev. Biol. Animal, 30-440-448 (2003).

Sung, et al., "Adhesiveness of Human Ligament Fibroblasts to Laminin", Journal of Orthopaedic Research, 13:166-173 (1995).

Zhou, et al., "Long-term nonpassaged EGF-responsive neural precursor cells are stem cells", Wound Repair and Regeneration, vol. 6, No. 4, pp. 337-348, 1998.

Adamczyk, et al., "Application of Surface Plasmon Resonance toward Studies of Low-Molecular-Weight Antigen-Antibody Binding Interactions", Methods, 20, pp. 319-328 (2000).

Marquart, "Immobilization Techniques", SPR pages [online] Jan. 2004, pp. 1-7.

Zhang, et al., "Use of surface plasmon resonance for the measurement of low affinity binding interactions between HSP72 and measles virus nucleocapsid protein", Biol. Proced. Online 2003;5(1):170-181.

Gestwicki, et al., "Using Receptor Conformational Change to Detect Low Molecular Weight Analytes by Surface Plasmon Resonance", Anal. Chem., 2001, 4, 5732-5737.

International Search Report dated Jul. 15, 2008, for PCT application serial No. PCT/US08/60951.

English machine translation only of JP 1993-228946 Sep. 7, 1993.

U.S. Appl. No. 12/171,475, filed Jul. 11, 2008.

U.S. Appl. No. 12/335,393, filed Dec. 15, 2008.

International Search Report for corresponding application No. PCT/US09/30412 dated Jan. 8, 2009.

Wawro, et al., "Optical fiber endface biosensor based on resonances in dielectric waveguide gratings", Biomedical Diagnostic Guidance and Surgical-Assist Systems II, Vo-Dihn et al eds., Proceedings of SPIE, vol. 3911, p. 86-94 (2000).

Torbin, et al., "The use of polymerizing cements for making replicas of optical surfaces", Optical Technology, vol. 40, No. 3, p. 192-196 (1973).

Ramsden, et al., "Optical Method for Measurement of Number and Shape of Attached Cells in Real Time", Cytometry, vol. 19, pp. 97-102 (1995).

Li et al., "Measurement and Adhesion and Spreading Kinetics of Baby Hamster Kidney and Hybridoma Cells Using an Integrated Optical Method", Biotechnol. Prog., vol. 10, pp. 520-524 (1994).

International Search Report dated Jul. 2, 2010, for corresponding PCT application No. PCT/US2010/035152, filed May 17, 2010.

Cunningham et al., "Advantages and application of label-free detection assays in drug screening", Expert Opin. Drug Discov., 3(7):891-901 (2008).

Palmer, "Diffraction Gratings, The Crucial Dispersive Component", Spectroscopy, 10(2), pp. 14-15 (1995).

Bandell et al., "Noxious Cold Ion Channel TRPA1 is Activated by Pungent Compounds and Bradykinin" Neuron, vol. 41, pp. 849-957 (2004).

Cunningham et al., "Label-Free Assays on the Bind System", Journal of Biomolecular Screening, 9:481 (2004).

IMT Applied Optics, "Resonant Grating Filters", 2008.

Cunningham et al., "Advantages and application of label-free detection assays in drug screening", Expert Opin. Drug Discovery, 3:891-901 (2008).

Comley, "Label-Free Detection New biosensors facilitate boarder range of drug discovery applications", Drug Discovery World Winter, p. 63-74 (May 2004).

Cooper, "Current biosensor technologies in drug discovery", Drug Discovery World Summer, p. 68-82 (2006).

Cunningham et al., "Colormetric Resonant Reflection as a Direct Biochemical Assay Technique", IEEE, Annual International Conference on Micro Electro Mechanical Systems, MEMS, Las Vegas, NV, Jan. 20-24, 2002.

Cunningham et al., "Label-Free Assays on the Bind System", Journal of Biomolecular Screening 9(6):481-490 (2004).

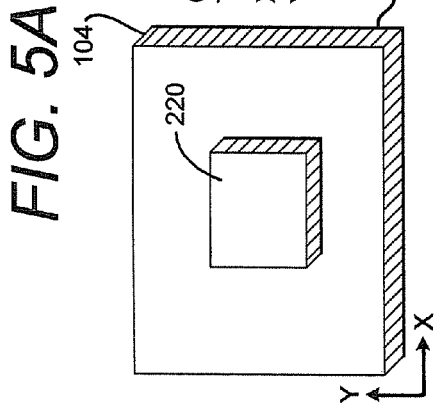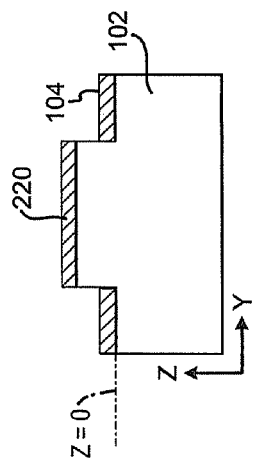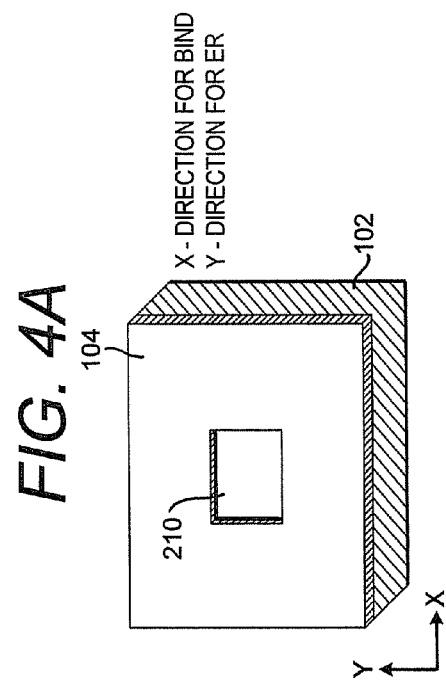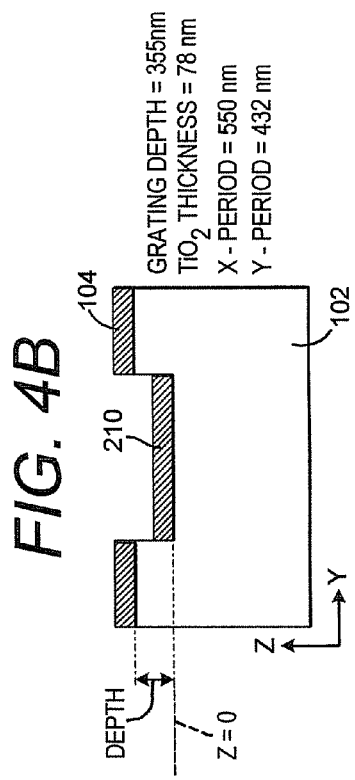

CELL CAPTURE ON THE BIND BIOSENSOR™ VIA AN IMMOBILIZED

NON-CAPTURE OF CELLS BY ANTI-MOUSE

CELL CAPTURE BLOCKED BY SOLUBLE Ag

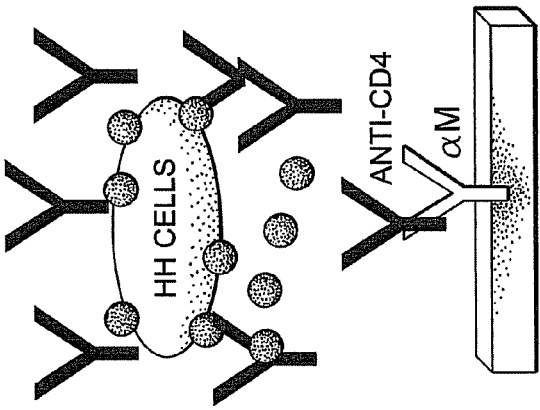
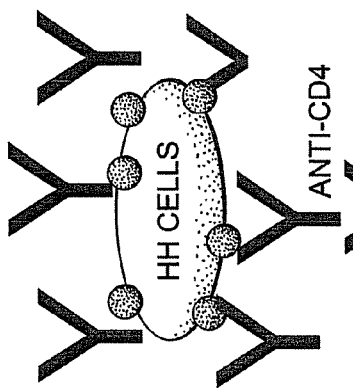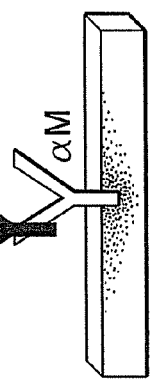
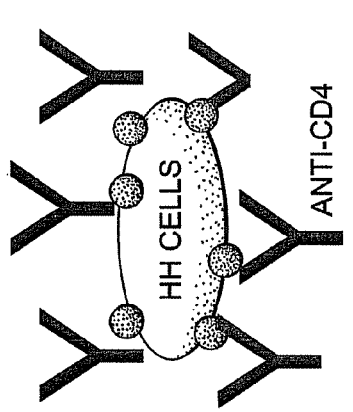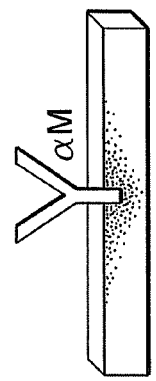

| Identity of IgG | Conc. of IgG | IgG (pm) | Antigen (pm) | Ratio* [Ag/IgG] | Identity of IgG | Conc. of IgG | IgG (pm) | Antigen (pm) | Ratio* [Ag/IgG] |
|---|---|---|---|---|---|---|---|---|---|
| LEX-1 | 20.00 | 189 | 107 | 0.57 | Lex-9 | 20.00 | 165 | 111 | 0.67 |
|  | 10.00 | 196 | 93 | 0.48 |  | 10.00 | 194 | 116 | 0.60 |
|  | 5.00 | 179 | 82 | 0.46 |  | 5.00 | 163 | 101 | 0.62 |
|  | 2.50 | 143 | 93 | 0.65 |  | 2.50 | 138 | 82 | 0.59 |
|  | 1.25 | 95 | 61 | 0.64 |  | 1.25 | 75 | 41 | 0.54 |
|  | 0.63 | 54 | 23 | 0.43 |  | 0.63 | 25 | 38 | 1.55 |
| LEX-2 | 20.00 | 184 | 124 | 0.68 | IgG-1 (neg) | 20.00 | 191 | -16 | -0.09 |
|  | 10.00 | 160 | 96 | 0.60 |  | 10.00 | 180 | 30 | 0.17 |
|  | 5.00 | 137 | 94 | 0.69 |  | 5.00 | 175 | 30 | 0.17 |
|  | 2.50 | 109 | 89 | 0.82 |  | 2.50 | 158 | 34 | 0.21 |
|  | 1.25 | 28 | 59 | 2.16 |  | 1.25 | 114 | 21 | 0.18 |
|  | 0.63 | 35 | 4 | 0.10 |  | HAT | 0 | 3 |  |

The cutoff for signal above background is 50 pm for IgGs and 30 pm for antigen.

|        | Ratio (GA1 0048) |          |          |      |        |                  |
|--------|------------------|----------|----------|------|--------|------------------|
| Ab     | aM-D             | aM-E (1) | aM-F (2a)| Avg  | ST Dev | % Theor Ratio    |
| LEX-9  | 0.72             | 0.78     |          | 0.74 | 0.03   | 61.9             |
| LEX-7  | 0.56             |          | 0.77     | 0.74 | 0.17   | 61.5             |
| LEX-6  | 0.62             |          | 0.68     | 0.73 | 0.13   | 60.6             |
| LEX-3  | 0.64             | 0.62     |          | 0.65 | 0.03   | 54.1             |
| LEX-10 | 0.57             | 0.65     |          | 0.62 | 0.05   | 51.9             |
| LEX-8  | 0.52             | 0.61     |          | 0.57 | 0.04   | 47.3             |
| LEX-2  | 0.49             | 0.56     |          | 0.53 | 0.04   | 44.0             |
| LEX-1  | 0.45             | 0.49     |          | 0.48 | 0.03   | 40.4             |
| LEX-5  | 0.18             | 0.23     |          | 0.22 | 0.03   | 18.1             |
| IgG-1  | 0.00             | 0.04     |          | 0.03 | 0.02   | 2.5              |
| LEX-4  | 0.02             | 0.02     |          | 0.02 | 0.01   | 1.7              |

Figure 14A

|        | Ratio (GA1 0049) |          |          |      |        |                  |
|--------|------------------|----------|----------|------|--------|------------------|
| Ab     | aM-D             | aM-E (1) | aM-F (2a)| Avg  | ST Dev | % Theor Ratio    |
| LEX-9  | 0.76             | 0.68     |          | 0.67 | 0.09   | 56.1             |
| LEX-10 | 0.67             | 0.68     |          | 0.67 | 0.01   | 55.8             |
| LEX-7  | 0.53             |          | 0.74     | 0.66 | 0.11   | 55.0             |
| LEX-3  | 0.57             | 0.67     |          | 0.60 | 0.06   | 50.2             |
| LEX-6  | 0.45             |          | 0.67     | 0.59 | 0.12   | 49.2             |
| LEX-8  | 0.44             | 0.58     |          | 0.53 | 0.07   | 44.1             |
| LEX-1  | 0.48             | 0.54     |          | 0.51 | 0.03   | 42.3             |
| LEX-2  | 0.40             | 0.51     |          | 0.47 | 0.06   | 39.0             |
| LEX-5  | 0.13             | 0.34     |          | 0.21 | 0.11   | 17.6             |
| IgG-1  | -0.03            | 0.07     |          | 0.03 | 0.05   | 2.5              |
| LEX-4  | 0.01             | 0.07     |          | 0.02 | 0.05   | 1.3              |

Figure 14B

|  | Biacore Screen | ELISA EC50 | % Theoretical Ratio | | Ratio Groups |
|---|---|---|---|---|---|
| Ab | nM | pM | GA1-48 | GA1-49 | |
| LEX-1 | 10 - 50 | 13 | 40.4 | 42.3 | 3 |
| LEX-2 | 10 - 50 | 13 | 44.0 | 39.0 | 3 |
| LEX-3 | | | 54.1 | 50.2 | 4 |
| LEX-4 | | | 1.7 | 1.3 | 1 |
| LEX-5 | 1000 | 150 | 18.1 | 17.6 | 2 |
| LEX-6 | | 13 | 60.6 | 49.2 | 4 |
| LEX-7 | 10 - 50 | 51 | 61.5 | 55.0 | 4 |
| LEX-8 | | | 47.3 | 44.1 | 3 |
| LEX-9 | <10 | 13 | 61.9 | 56.1 | 4 |
| LEX-10 | <10 | 25 | 51.9 | 55.8 | 4 |

|   | 1   | 2  | 3   | 4   | 5      | 6   |
|---|-----|----|-----|-----|--------|-----|
| A | 13  | 73 | -12 | 86  | -32    | -10 |
| B | -2  | 74 | 1   | -9  | -27    | 70  |
| C | -3  | 63 | 20  | 170 | 1      | 129 |
| D | 27  | 84 | -3  | 29  | -6     | 0   |
| E | -6  | -5 | -5  | 103 | 89     | -22 |
| F | -2  | -6 | -1  | -8  | -8     | -16 |
| G | -5  | 82 | 117 | 25  | -8     | 97  |
| H | 150 | -1 | 120 | 5   | -6     | 168 |
|   |     |    |     |     | NO IgG | POS |

| A | HAT | | | PBS | | | Average Ratio across both Assays (N=4) | Biacore (Screening) nM |
|---|---|---|---|---|---|---|---|---|
| | Ab (pm) | Ag (pm) | Ratio Ag/Ab | Ab (pm) | Ag (pm) | Ratio Ag/Ab | | |
| LEX-9 | 105 | 94 | 0.90 | 133 | 83 | 0.62 | 0.75 + 0.16 | <10 |
| | 106 | 92 | 0.87 | 133 | 78 | 0.59 | | |
| LEX-7 | 116 | 70 | 0.60 | 126 | 71 | 0.56 | 0.58 + 0.03 | 10-50 |
| | 115 | 71 | 0.61 | 129 | 72 | 0.55 | | |
| LEX-10 | 100 | 59 | 0.59 | 143 | 70 | 0.49 | 0.53 + 0.06 | <10 |
| | 100 | 57 | 0.57 | 149 | 68 | 0.46 | | |
| LEX-6 | 119 | 63 | 0.52 | 136 | 72 | 0.53 | 0.52 + 0.02 | |
| | 122 | 61 | 0.50 | 134 | 70 | 0.52 | | |
| LEX-2 | 101 | 52 | 0.51 | 131 | 66 | 0.50 | 0.49+ 0.03 | 10 - 50 |
| | 107 | 47 | 0.44 | 132 | 66 | 0.50 | | |
| LEX-1 | 115 | 57 | 0.50 | 132 | 66 | 0.50 | 0.49 +0.03 | 10 - 50 |
| | 114 | 51 | 0.44 | 131 | 66 | 0.51 | | |
| LEX-4 | 123 | 6 | 0.05 | 123 | 16 | 0.13 | 0.09 + 0.06 | |
| | 127 | 4 | 0.03 | 126 | 18 | 0.14 | | |
| IgG-1 | 121 | 7 | 0.05 | 139 | 10 | 0.07 | 0.07 + 0.01 | |

| | IgG (2 × 90 kDa) / 150 kDa = 1.2 | | | | Soluble F(ab) Fragment (1 × 90 kDa) / 50 kDa = 1.8 | |
|---|---|---|---|---|---|---|
| | GA1 0021 αH-G (Fc specific) | | GA1 0050 αH-H (Fab specific) | | αH-H (Fab specific) | |
| | Empirical Ratio | % Theor Ratio | Empirical Ratio | % Theor Ratio | Empirical Ratio | % Theor Ratio |
| CH31 | | | 0.19 ± 0.00 | 16 | 0.07 ± 0.13 | 6 |
| LEX-11 | 0.71 ± 0.16 | 59 | 0.73 ± 0.08 | 61 | | |
| LEX-12 | 0.51 ± 0.15 | 43 | 0.35 | 29 | 0.83 ± 0.05 | 46 |
| LEX-13 | | | 0.40 | 33 | | |
| LEX-14 | 0.46 ± 0.05 | 38 | 0.50 ± 0.02 | 42 | 0.24 ± 0.04 | 13 |
| LEX-15 | 0.57 ± 0.05 | 48 | 0.42 ± 0.05 | 35 | 0.90 ± 0.19 | 50 |

| A | IgG-I | | | | | | | | |
|---|---|---|---|---|---|---|---|---|---|
| | LEX-20 | | | LEX-21 | | | LEX-22 (neg) | | |
| Antigen Type | PBST | His-FL | Fc-Dm2 | PBST | His-FL | Fc-Dm2 | PBST | His-FL | Fc-Dm2 |
| IgG I (pm) | 185 | 185 | 181 | 185 | 194 | 200 | 180 | 184 | 179 |
| Antigen (pm) | 4 | 84 | 36 | 5 | 78 | 133 | -3 | -2 | 19 |
| LEX-20 (pm) | 9 | 12 | 2 | 11 | 21 | 1 | 18 | 17 | 14 |
| IgG I (pm) | 189 | 185 | 202 | 213 | 216 | 207 | 194 | 190 | 194 |
| Antigen (pm) | -2 | 87 | 38 | -5 | 75 | 128 | 4 | -2 | 21 |
| LEX-21 (pm) | 16 | 22 | 12 | 14 | 20 | 6 | 15 | 23 | 23 |
| IgG I (pm) | 190 | 186 | 188 | 192 | 197 | 186 | 180 | 183 | 191 |
| Antigen (pm) | 8 | 87 | 39 | 1 | 85 | 132 | 0 | -3 | 22 |
| LEX-22 (pm) (neg) | 2 | 2 | -5 | 5 | 8 | -7 | 8 | 15 | 2 |
| IgG I | 192 | 182 | 190 | 197 | 206 | 201 | 190 | 181 | 203 |
| Antigen (pm) | -6 | 89 | 38 | -2 | 82 | 131 | -2 | 0 | 19 |
| LEX-30 (pm) | 6 | 44 | 12 | 6 | 40 | 93 | 1 | 5 | 9 |
| IgG I (pm) | 181 | 180 | 187 | 198 | 194 | 202 | 181 | 178 | 200 |
| Antigen (pm) | -4 | 87 | 36 | 1 | 83 | 134 | 2 | 6 | 20 |
| LEX-31 (pm) | 5 | 8 | -2 | -3 | 6 | -6 | -2 | 1 | 0 |

Figure 20

| IgG | Fold over Background | IgG | Fold over Background | IgG | Fold over Bkgrd | IgG | Fold over Background |
|---|---|---|---|---|---|---|---|
| LEX-30 | 1.8 | LEX-31 | 8.5 | LEX-42 | 0.8 | LEX-24 | 32.0 |
| LEX-33 | 10.9 | LEX-37 | 6.5 | LEX-43 | 11.8 | LEX-22 (neg) | -4.7 |
| LEX-34 | 1.7 | LEX-38 | 2.3 | LEX-44 | 4.4 | LEX-45 | 8.2 |
| LEX-35 | 1.1 | LEX-39 | 3.1 | LEX-23 | 47.4 | IgG-1 | 3.3 |
| LEX-32 | 2.1 | LEX-40 | 3.6 | LEX-20 | 67 | | |
| LEX-36 | 8.2 | LEX-41 | 10.4 | LEX-21 | 128.3 | | |

Figure 21

METHODS FOR SCREENING CELLS AND ANTIBODIES

PRIORITY

This application is a divisional application of U.S. Ser. No. 12/758,928, filed Apr. 13, 2010, now U.S. Pat. No. 8,202,735, which is a divisional application of U.S. Ser. No. 11/635,934, filed Dec. 8, 2006, now U.S. Pat. No. 7,927,822, which is a continuation in part of U.S. Ser. No. 10/667,696, filed Sep. 22, 2003, now U.S. Pat. No. 7,264,973, which is a continuation in part of U.S. Ser. No. 10/237,641, filed Sep. 9, 2002, now U.S. Pat. No. 7,153,702. U.S. Ser. No. 11/635,934, filed Dec. 8, 2006, is also a continuation in part of U.S. Ser. No. 11/490,556, filed on Jul. 20, 2006, which claims the benefit of the following applications: U.S. Ser. No. 60/707,579, filed Aug. 11, 2005; U.S. Ser. No. 60/713,694 filed Sep. 2, 2005; U.S. Ser. No. 60/778,160, filed Feb. 28, 2006; and U.S. Ser. No. 60/790,207 filed Apr. 7, 2006. All of these applications are incorporated herein by reference in their entirety.

BACKGROUND OF THE INVENTION

It has been estimated that at least two days of laboratory time and the use of fluorescent labels are required to assess cellular changes upon exposure to biological entities. See, e.g., Dharmawardhane et al., 1997, J. Cell Biol. 138(6):1265-78. Additionally, it has been estimated that at least 8-24 hours of laboratory time and the use of a secondary dye are required to quantify total cell movement or cell changes toward biological entities, such as a protein, peptide or small molecule. See, Reckless & Grainger. 1999. *Biochem. J.* 340: 803-811, Taguchi et al. 1998. *J. Exp. Med.* 187(12): 1927-1940, Jackson et al. 1999. *J. Pharm. & Exper. Therapeutics.* 288(1): 286-294 and Yarrow et al., 2004 *BMC Biotechnol.* 4(21):1-9.

Monoclonal antibodies are produced by hybrid myeloma or hybridoma cell lines (referred to herein as "hybridomas"). Screening of hybridoma supernatants for antibodies that specifically bind a protein target is a critical step of monoclonal antibody production. Many thousands of myeloma cells and mouse spleen cells are fused together and grown together in HAT selective medium. Only hybrid cells containing the DNA of both types of cells are able to grow and therefore produce IgGs. The supernatant of the mixture of these cells is screened to determine if any of the cells in the mixture produce an antibody that specifically binds a protein target.

ELISA assays can be used for the screening of this complex mixture of antibodies. However, ELISAs are time consuming and are often qualitative. Additionally, an isolated protein used to capture the antibodies on an ELISA plate may not appropriately mimic the true protein found, e.g., on the surface of a cell. The isolated protein may have a different folding conformation, be situated on the ELISA plate so that parts other protein are not available for binding to antibodies, or have any number of other sterically or chemically related inhibition issues. Antibodies identified using ELISA screening may have very little affinity for the natively folded protein on, e.g., a cell surface. Unfortunately, this information will not be apparent for several weeks. Furthermore, antibody selection processes are not able to discern specific desired biological activity against the target by antibody binding until late in the process in other complex assay formats. Methods are needed to reduce the time to perform these assays.

SUMMARY OF THE INVENTION

One embodiment of the invention provides a method of detecting a change in a cell growth pattern. The method comprises applying one or more cells to a location on a surface of a colorimetric resonant reflectance optical biosensor; detecting a colorimetric resonant reflectance optical peak wavelength value (PWV) for the location; incubating the one or more cells for a period of time or applying a test reagent to the one or more cells and incubating the one or more cells for a period of time; detecting the colorimetric resonant reflectance optical PWV for the location; and comparing the PWVs. A difference between the first colorimetric resonant reflectance optical PWV in relation to the second colorimetric resonant reflectance optical PWV indicates a change in the cell growth pattern in the one or more cells. The change in cell growth pattern can be a change in cell morphology, change in cell adhesion, change in cell migration, change in cell proliferation, change in cell death, change in microtubule structure, change in microfilament structure, granule exocytosis, respiratory burst, cell differentiation, or a combination thereof. The PWVs can be detected using a scanner with a lens having a lower limit pixel size of about 2 micrometers to about 15 micrometers. The location on the surface of a colorimetric resonant reflectance optical biosensor can be an internal surface of a vessel selected from the group consisting of a microtiter well, microtiter plate, test tube, Petri dish, microfluidic channel, and microarray.

Another embodiment of the invention provides a method of screening about 100 or more different antibodies in one receptacle. The method comprises immobilizing the antibodies to a colorimetric resonant reflectance biosensor, wherein the colorimetric resonant reflectance biosensor comprises an inner surface of the receptacle; determining a first peak wavelength value for the receptacle; adding one or more natively folded proteins to the receptacle; determining a second peak wavelength value for the receptacle; and comparing the first and second peak wavelength values. If the second peak wavelength value is higher than the first peak wavelength value, then one or more immobilized antibodies in the receptacle have specifically bound the one or more natively folded proteins. The total antibody concentration in the receptacle can be greater than 2 mg/ml. The one or more antibodies in the receptacle that have specifically bound the one or more natively folded proteins can be present at a concentration of less than 5 ng/ml. The natively folded protein can be a cell surface protein. The natively folded protein can be part of a whole cell that is added to the receptacle. The cell can be pre-treated with one or more antibodies prior to the cell being added to the receptacle. The antibodies can be produced by about 100, 1,000 or more different hybridoma cells.

Even another embodiment of the invention provides a method of detecting specific binding of a first antibody to a protein, wherein the antibody is in a mixture of more than 100 different antibodies, wherein the first antibody is in the mixture of antibodies at a concentration of less than about 3 ng/ml, and wherein the concentration of the mixture of antibodies is greater than about 3 ug/ml. The method comprises immobilizing the mixture of antibodies to a colorimetric resonant reflectance biosensor, wherein the colorimetric resonant reflectance biosensor comprises an inner surface of the receptacle; determining a first peak wavelength value for the receptacle; adding one or more proteins to the receptacle, wherein one or more of the proteins may specifically bind to the first antibody; determining a second peak wavelength value for the receptacle; comparing the first and second peak wavelength values. If the second peak wavelength value is higher than the first peak wavelength value, then one or more antibodies in the receptacle have specifically bound the one or more of the proteins.

A further embodiment of the invention provides a method of screening about 100 or more different antibodies in one receptacle. The method comprises immobilizing the antibodies to a biosensor comprising a substrate having a periodic surface grating structure wherein the periodic grating structure is constructed in a manner designed for both 1) optical interrogation of the biosensor with light in an evanescent resonance (ER) detection mode, and 2) optical interrogation of the biosensor with light in a label-free detection mode, wherein the biosensor comprises an inner surface of the receptacle; adding one or more cells to the receptacle; illuminating the biosensor in a readout detection instrument with light from at least one light source designed for the ER detection mode and illuminating the sensor with the at least one light source designed for the label-free detection mode; and analyzing light reflected from the biosensor. The label-free detection mode can indicate that one or more cells have bound to the antibodies and the ER detection mode can indicate a biological activity of the one or more cells. The at least one light source can comprise a first label-free light source and a second ER lightsource, and the method can further comprise the step of selectively illuminating the sensor with light from the first and second light sources. The grating structure can comprise a two-dimensional grating structure wherein: the first dimension of the periodic grating structure comprises a grating structure designed for label-free detection, and the second dimension of the periodic grating structure comprises a grating structure designed for ER detection. The grating structure can further comprise a substrate, a layer applied to the substrate having a grating structure, an intermediate $SiO_2$ layer deposited on the layer having the grating structures, and a layer of relatively high index of refraction material deposited on the $SiO_2$ layer. The grating structure can further comprise a substrate, a layer applied to the substrate having the grating structures in the first and second dimensions, an intermediate $SiO_2$ layer deposited on the layer having the grating structures, and a layer of relatively high index of refraction material deposited on the $SiO_2$ layer. The $SiO_2$ layer has a thickness of between about 500 and 5000 Angstroms. The grating structure in the first dimension can have a period of between 260 and about 1500 nm and a depth of the grating can be between about 100 nm and about 3000 nm, and the grating structure in the second dimension can be between about 200 nm and about 1000 nm, and the depth of the grating in the second dimension can between about 10 nm and about 300 nm.

Still another embodiment of the invention provides a method of detecting specific binding of a first antibody to unpurified cells or unpurified antigen. The method comprises immobilizing the first antibody to a colorimetric resonant reflectance biosensor; detecting a first peak wavelength value; adding the unpurified cells or unpurified antigen to the colorimetric resonant reflectance biosensor; detecting a second peak wavelength value; and comparing the first and second peak wavelength values. An increase in the second peak wavelength value indicates specific binding of the first antibody to the unpurified cells or unpurified cells. A first antigen specific for the first antibody can be added to the unpurified cells or unpurified antigen prior to adding the unpurified cells or unpurified antigen to the colorimetric resonant reflectance biosensor, and wherein a lower second peak wavelength value than the second peak wavelength value indicates specific binding of the unpurified cells or unpurified antigen to the first antigen. A second antibody having the same specificity as the first antibody can be added to the unpurified cells or unpurified antigen prior to adding the unpurified cells or unpurified antigen to the colorimetric resonant reflectance biosensor. A lower second peak wavelength value than the second peak wavelength value indicates specific binding of the unpurified cells or unpurified antigen to the second antibody. The unpurified cells can be about 10,000 or fewer cells. The concentration of the first antibody can be about 3 ng/ml or less. The unpurified cells can be present in HAT media, hybridoma media, or cell culture media. The first antibody, unpurified cells, and unpurified antigen can not have detection labels.

Another embodiment of the invention provides a method of ranking antibodies according to their affinity for an antigen. The method comprises immobilizing a specific amount of one or more types of antibodies to a colorimetric resonant reflectance biosensor such that each type of antibody is present at a separate location; determining a first peak wavelength value for each separate location; adding antigens or cells comprising cell surface antigens to the colorimetric resonant reflectance biosensor, determining a second peak wavelength value for each separate location; comparing the first and second peak wavelength values to determine the ranking of antibodies. The cells comprising cell surface antigens can be unpurified cells. The cells comprising cell surface antigens can be about 10,000 or less cells. The one or more types of antibodies can be present at a concentration of 3 ng/ml or less. The one or more types of antibodies can be unpurified antibodies. The antibodies can be present in hybridoma media, HAT media, or cell culture media. The one or more types of antibodies are 96 or more types of antibodies that are present at 96 or more separate locations on the colorimetric resonant reflectance biosensor.

Even another embodiment of the invention provides a method of determining whether different types of antibodies that are each specific for a first antigen bind to the same region of the first antigen. The method comprises: immobilizing the first antibody to a colorimetric resonant reflectance biosensor; adding the first antigen to the colorimetric resonant reflectance biosensor; determining a first peak wavelength value; adding the second antibody to the colorimetric resonant reflectance biosensor; determining a second peak wavelength value and comparing the first and second peak wavelength values. If the first and second antibodies bind different regions of the first antigen, then the first and second antibodies bind to different regions of the first antigen. The first and second antibodies can be present at a concentration of 3 ng/ml or less. The first and second antibodies can be unpurified antibodies. The antibodies can be present in hybridoma media, HAT media, or cell culture media.

Therefore, the instant invention provides compositions and methods to quickly and easily assess cellular changes and to screen complex mixtures of antibodies.

BRIEF DESCRIPTION OF THE DRAWINGS

FIGS. 4A-4B are perspective and cross-sectional views, respectively, of a two-dimensional grating design characterized by periodic holes in a grating structure which is optimized for BIND™ (label-free) detection in a water environment when illuminated by X polarized light and optimized for ER detection in an air environment when illuminated by Y polarized light.

FIGS. 5A-5B show perspective and cross-sectional views, respectively, of a two-dimensional grating design characterized by periodic posts in a grating structure which is optimized in one direction for BIND™ (label-free) detection in a water environment when illuminated by X polarized light and optimized for ER detection in an air environment when illuminated by Y polarized light.

FIGS. 8A-H shows cell based competition assays. Panels A-F show the differing conditions used in the assays. Panels G and H show the results of the assays.

FIGS. 14A-C demonstrate the reproducibility of ranking of mouse IgGs in HAT medium.

FIG. 15 demonstrates that the subclass and the ranking of antibodies can be done simultaneously.

FIG. 16 demonstrates the detection of mouse IgGs from a limited dilution of a hybridoma clone.

FIG. 17 shows a comparison of the rank of mouse IgGs in crude and purified assays.

FIG. 18 shows a comparison of the rank of human IgGs and F(ab)s in crude and purified assays.

FIG. 20 shows an antibody binning assay to find sandwich pairs.

FIG. 21 shows an antibody binning assay to find sandwich pairs.

DETAILED DESCRIPTION OF THE INVENTION

Figure 1A:
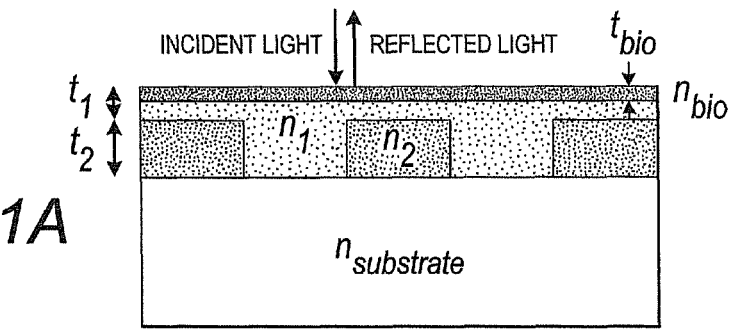
FIG. 1A shows a cross-sectional view of a colorimetric resonant reflectance biosensor wherein light is shown as illuminating the bottom of the biosensor; however, light can illuminate the biosensor from either the top or the bottom.

One embodiment of the invention allows the direct detection of cell changes as they occur in real time with a colorimetric resonant reflectance biosensor and without the need to incorporate or without interference from radiometric, colorimetric, or fluorescent labels. Changes in cell behavior and morphology can be detected as the cell is perturbed. The cellular changes can then be detected in real time using a high speed, high resolution instrument, such as the BIND Scanner™ (i.e., a colorimetric resonant reflectance biosensor system), and corresponding algorithms to quantify data. See, e.g., U.S. Pat. No. 6,951,715 and U.S. Pat. Publ. 2004/0151626. By combining this methodology, instrumentation and computational analysis, cellular behavior can be expediently monitored in real time, in a label free manner.

Colorimetric resonant reflectance biosensors, such as SRU Biosystems, Inc. BIND™ technology (Woburn, Mass.) have the capability of measuring changes to a surface with respect to mass attachment from nanoscale biological systems. The applications and the methods, in which colorimetric resonant reflectance biosensors have been previously implemented, have changed as the resolution of the instruments has improved. Previously, measurement of the quantity of cells attached to the colorimetric resonant reflectance biosensor surface was the primary goal. While looking at some poorer resolution images of cells, however, it was noted that cells gave differential signals with respect to the number of pixels occupied, intensity of signal/pixel, change in PWV of each pixel, etc. While trying to reduce the variability of these data, it became clear that the variability lay within the individual cells and their differential morphological responses to stimuli. To further investigate these cellular events, a higher resolution version of a BIND Scanner™ (i.e., a colorimetric resonant reflectance biosensor system), was constructed. The scanner has a higher resolution lens than previously used scanners. The lens has a lower limit pixel size of about 7 micrometers. Additionally, a methodology was developed for analyzing cell changes in real time at better resolution.

Biosensors

Biosensors of the invention can be colorimetric resonant reflectance biosensors. See e.g., Cunningham et al., "Colorimetric resonant reflection as a direct biochemical assay technique," Sensors and Actuators B, Volume 81, p. 316-328, Jan. 5, 2002; U.S. Pat. Publ. No. 2004/0091397. Colorimetric resonant biosensors are not surface plasmon resonant (SPR) biosensors. SPR biosensors have a thin metal layer, such as silver, gold, copper, aluminum, sodium, and indium. The metal must have conduction band electrons capable of resonating with light at a suitable wavelength. A SPR biosensor surface exposed to light must be pure metal. Oxides, sulfides and other films interfere with SPR. Colorimetric resonant biosensors do not have a metal layer, rather they have a dielectric coating of high refractive index material, such as $TiO_2$.

Grating-based waveguide biosensors are described in, e.g., U.S. Pat. No. 5,738,825. A grating-based waveguide biosensor comprises a waveguiding film and a diffraction grating that incouples an incident light field into the waveguiding film to generate a diffracted light field. A change in the effective refractive index of the waveguiding film is detected. Devices where the wave must be transported a significant distance within the device, such as grating-based waveguide biosensors, lack the spatial resolution of the current invention.

A colorimetric resonant reflectance biosensor allows biochemical interactions to be measured on the biosensor's surface without the use of fluorescent tags, colorimetric labels or any other type of detection tag or detection label. A biosensor surface contains an optical structure that, when illuminated with collimated and/or white light, is designed to reflect only a narrow band of wavelengths ("a resonant grating effect"). The narrow wavelength band is described as a wavelength "peak." The "peak wavelength value" (PWV) changes when materials, such as biological materials, are deposited or removed from the biosensor surface. A readout instrument is used to illuminate distinct locations on a biosensor surface with collimated and/or white light, and to collect reflected light. The collected light is gathered into a wavelength spectrometer for determination of a PWV.

A biosensor can be incorporated into standard disposable laboratory items such as microtiter plates by bonding the structure (biosensor side up) into the bottom of a bottomless microtiter plate cartridge. Incorporation of a biosensor into common laboratory format cartridges is desirable for compatibility with existing microtiter plate handling equipment such as mixers, incubators, and liquid dispensing equipment. Colorimetric resonant reflectance biosensors can also be incorporated into, e.g., microfluidic, macrofluidic, or microarray devices (see, e.g., U.S. Pat. No. 7,033,819, U.S.

Pat. No. 7,033,821). Colorimetric resonant reflectance biosensors can be used with well-know methodology in the art (see, e.g., *Methods of Molecular Biology* edited by Jun-Lin Guan, Vol. 294, Humana Press, Totowa, N.J.) to monitor cell behavioral changes or the lack of these changes upon exposure to one or more extracellular reagents.

Colorimetric resonant reflectance biosensors comprise subwavelength structured surfaces (SWS) and are an unconventional type of diffractive optic that can mimic the effect of thin-film coatings. (Peng & Morris, "Resonant scattering from two-dimensional gratings," *J. Opt. Soc. Am. A*, Vol. 13, No. 5, p. 993, May 1996; Magnusson, & Wang, "New principle for optical filters," *Appl. Phys. Lett.*, 61, No. 9, p. 1022, August, 1992; Peng & Morris, "Experimental demonstration of resonant anomalies in diffraction from two-dimensional gratings," *Optics Letters*, Vol. 21, No. 8, p. 549, April, 1996). A SWS structure contains a one-dimensional, two-dimensional, or three dimensional grating in which the grating period is small compared to the wavelength of incident light so that no diffractive orders other than the reflected and transmitted zeroth orders are allowed to propagate. Propagation of guided modes in the lateral direction are not supported. Rather, the guided mode resonant effect occurs over a highly localized region of approximately 3 microns from the point that any photon enters the biosensor structure.

The reflected or transmitted light of a colorimetric resonant reflectance biosensor can be modulated by the addition of molecules such as specific binding substances or binding partners or both to the upper surface of the biosensor. The added molecules increase the optical path length of incident radiation through the structure, and thus modify the wavelength at which maximum reflectance or transmittance will occur.

In one embodiment, a colorimetric resonant reflectance biosensor, when illuminated with white and/or collimated light, is designed to reflect a single wavelength or a narrow band of wavelengths (a "resonant grating effect"). When mass is deposited on the surface of the biosensor, the reflected wavelength is shifted due to the change of the optical path of light that is shown on the biosensor.

A detection system consists of, for example, a light source that illuminates a small spot of a biosensor at normal incidence through, for example, a fiber optic probe, and a spectrometer that collects the reflected light through, for example, a second fiber optic probe also at normal incidence. Because no physical contact occurs between the excitation/detection system and the biosensor surface, no special coupling prisms are required and the biosensor can be easily adapted to any commonly used assay platform including, for example, microtiter plates. A single spectrometer reading can be performed in several milliseconds, thus it is possible to quickly measure a large number of molecular interactions taking place in parallel upon a biosensor surface, and to monitor reaction kinetics in real time.

Figure 1B:
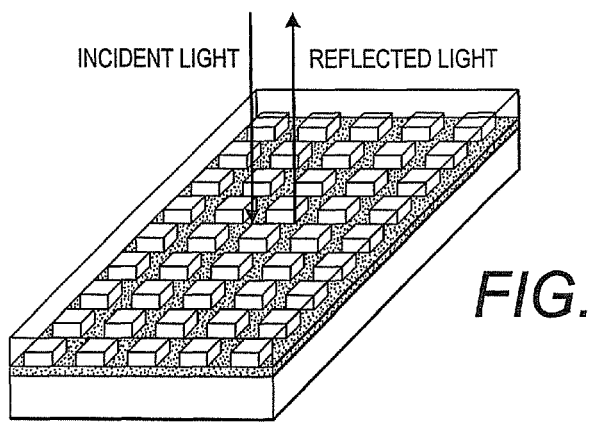
FIG. 1B shows a diagram of a colorimetric resonant reflectance biosensor wherein light is shown as illuminating the bottom of the biosensor; however, light can illuminate the biosensor from either the top or the bottom.

FIGS. 1A and 1B are diagrams of an example of a colorimetric resonant reflectance biosensor. In FIG. 1, $n_{substrate}$ represents a substrate material. $n_2$ represents the refractive index of an optical grating. $n_1$ represents an optional cover layer. $n_{bio}$ represents the refractive index of an optional biological material. $t_1$ represents the thickness of the optional cover layer above the one-, two- or three-dimensional grating structure. $t_2$ represents the thickness of the grating. $t_{bio}$ represents the thickness of the layer of the biological material. In one embodiment, are n2<n1 (see FIG. 1A). Layer thicknesses (i.e. cover layer, biological material, or an optical grating) are selected to achieve resonant wavelength sensitivity to additional molecules on the top surface. The grating period is selected to achieve resonance at a desired wavelength.

A colorimetric resonant reflectance biosensor comprises, e.g., an optical grating comprised of a high refractive index material, a substrate layer that supports the grating, and optionally one or more specific binding substances or linkers immobilized on the surface of the grating opposite of the substrate layer. The high refractive index material has a higher refractive index than a substrate layer. See, e.g., U.S. Pat. No. 7,094,595; U.S. Pat. No. 7,070,987. Optionally, a cover layer covers the grating surface. An optical grating is coated with a high refractive index dielectric film which can be comprised of a material that includes, for example, zinc sulfide, titanium dioxide, tantalum oxide, silicon nitride, and silicon dioxide. A cross-sectional profile of a grating with optical features can comprise any periodically repeating function, for example, a "square-wave." An optical grating can also comprise a repeating pattern of shapes selected from the group consisting of lines (one-dimensional), squares, circles, ellipses, triangles, trapezoids, sinusoidal waves, ovals, rectangles, and hexagons. A colorimetric resonant reflectance biosensor of the invention can also comprise an optical grating comprised of, for example, plastic or epoxy, which is coated with a high refractive index material.

Figure 2:
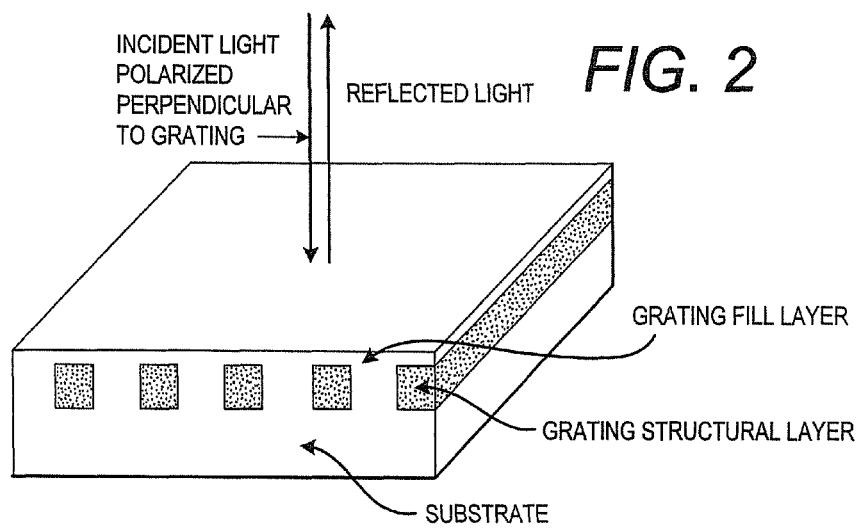
FIG. 2 shows an embodiment of a colorimetric resonant reflection biosensor comprising a one-dimensional grating.

Linear gratings (i.e., one dimensional gratings) have resonant characteristics where the illuminating light polarization is oriented perpendicular to the grating period. A schematic diagram of one embodiment a linear grating structure with an optional cover layer is shown in FIG. 2. A colorimetric resonant reflection biosensor can also comprise, for example, a two-dimensional grating, e.g., a hexagonal array of holes or squares. Other shapes can be used as well. A linear grating has the same pitch (i.e. distance between regions of high and low refractive index), period, layer thicknesses, and material properties as a hexagonal array grating. However, light must be polarized perpendicular to the grating lines in order to be resonantly coupled into the optical structure. Therefore, a polarizing filter oriented with its polarization axis perpendicular to the linear grating must be inserted between the illumination source and the biosensor surface. Because only a small portion of the illuminating light source is correctly polarized, a longer integration time is required to collect an equivalent amount of resonantly reflected light compared to a hexagonal grating.

An optical grating can also comprise, for example, a "stepped" profile, in which high refractive index regions of a single, fixed height are embedded within a lower refractive index cover layer. The alternating regions of high and low refractive index provide an optical waveguide parallel to the top surface of the biosensor.

A colorimetric resonant reflectance biosensor of the invention can further comprise a cover layer on the surface of an optical grating opposite of a substrate layer. Where a cover layer is present, the one or more specific binding substances are immobilized on the surface of the cover layer opposite of the grating. Preferably, a cover layer comprises a material that has a lower refractive index than a material that comprises the grating. A cover layer can be comprised of, for example, glass (including spin-on glass (SOG)), epoxy, or plastic.

For example, various polymers that meet the refractive index requirement of a biosensor can be used for a cover layer. SOG can be used due to its favorable refractive index, ease of handling, and readiness of being activated with specific binding substances using the wealth of glass surface activation techniques. When the flatness of the biosensor surface is not an issue for a particular system setup, a grating structure of SiN/glass can directly be used as the sensing surface, the activation of which can be done using the same means as on a glass surface.

Resonant reflection can also be obtained without a planarizing cover layer over an optical grating. For example, a biosensor can contain only a substrate coated with a structured thin film layer of high refractive index material. Without the use of a planarizing cover layer, the surrounding medium (such as air or water) fills the grating. Therefore, specific binding substances are immobilized to the biosensor on all surfaces of an optical grating exposed to the specific binding substances, rather than only on an upper surface.

In general, a colorimetric resonant reflectance biosensor of the invention will be illuminated with white and/or collimated light that will contain light of every polarization angle. The orientation of the polarization angle with respect to repeating features in a biosensor grating will determine the resonance wavelength. For example, a "linear grating" (i.e., a one-dimensional grating) biosensor consisting of a set of repeating lines and spaces will have two optical polarizations that can generate separate resonant reflections. Light that is polarized perpendicularly to the lines is called "s-polarized," while light that is polarized parallel to the lines is called "p-polarized." Both the s and p components of incident light exist simultaneously in an unfiltered illumination beam, and each generates a separate resonant signal. A biosensor can generally be designed to optimize the properties of only one polarization (the s-polarization), and the non-optimized polarization is easily removed by a polarizing filter.

In order to remove the polarization dependence, so that every polarization angle generates the same resonant reflection spectra, an alternate biosensor structure can be used that consists of a set of concentric rings. In this structure, the difference between the inside diameter and the outside diameter of each concentric ring is equal to about one-half of a grating period. Each successive ring has an inside diameter that is about one grating period greater than the inside diameter of the previous ring. The concentric ring pattern extends to cover a single sensor location—such as an array spot or a microtiter plate well. Each separate microarray spot or microtiter plate well has a separate concentric ring pattern centered within it. All polarization directions of such a structure have the same cross-sectional profile. The concentric ring structure must be illuminated precisely on-center to preserve polarization independence. The grating period of a concentric ring structure is less than the wavelength of the resonantly reflected light. The grating period is about 0.01 micron to about 1 micron. The grating depth is about 0.01 to about 1 micron.

In another embodiment, an array of holes or posts are arranged to closely approximate the concentric circle structure described above without requiring the illumination beam to be centered upon any particular location of the grid. Such an array pattern is automatically generated by the optical interference of three laser beams incident on a surface from three directions at equal angles. In this pattern, the holes (or posts) are centered upon the corners of an array of closely packed hexagons. The holes or posts also occur in the center of each hexagon. Such a hexagonal grid of holes or posts has three polarization directions that "see" the same cross-sectional profile. The hexagonal grid structure, therefore, provides equivalent resonant reflection spectra using light of any polarization angle. Thus, no polarizing filter is required to remove unwanted reflected signal components. The period of the holes or posts can be about 0.01 microns to about 1 micron and the depth or height can be about 0.01 microns to about 1 micron.

A detection system can comprise a colorimetric resonant reflectance biosensor a light source that directs light to the colorimetric resonant reflectance biosensor, and a detector that detects light reflected from the biosensor. In one embodiment, it is possible to simplify the readout instrumentation by the application of a filter so that only positive results over a determined threshold trigger a detection.

By measuring the shift in resonant wavelength at each distinct location of a colorimetric resonant reflectance biosensor of the invention, it is possible to determine which distinct locations have, e.g., biological material deposited on them. The extent of the shift can be used to determine, e.g., the amount of binding partners in a test sample and the chemical affinity between one or more specific binding substances and the binding partners of the test sample.

A colorimetric resonant reflectance biosensor can be illuminated twice. The first measurement determines the reflectance spectra of one or more distinct locations of a biosensor with, e.g., no biological material on the biosensor. The second measurement determines the reflectance spectra after, e.g., one or more cells are applied to a biosensor. The difference in peak wavelength between these two measurements is a measurement of the presence or amount of cells on the biosensor. This method of illumination can control for small imperfections in a surface of a biosensor that can result in regions with slight variations in the peak resonant wavelength. This method can also control for varying concentrations or density of cell matter on a biosensor.

Surface of Biosensor

One or more cells can be immobilized on a biosensor by for example, physical adsorption or by chemical binding. A cell can specifically bind to a biosensor surface via a specific binding substance such as a nucleic acid, peptide, protein solution, peptide solution, solutions containing compounds from a combinatorial chemical library, antigen, polyclonal antibody, monoclonal antibody, single chain antibody (scFv), F(ab) fragment, F(ab')$_2$ fragment, Fv fragment, small organic molecule, virus, polymer or biological sample, wherein the specific binding substance is immobilized to the surface of the biosensor and the binding partner is on the surface of the cell.

Furthermore, cells can be arranged in an array of one or more distinct locations on the biosensor surface, said surface residing within one or more wells of a multiwell plate and comprising one or more surfaces of the multiwell plate or microarray. The array of cells comprises one or more cells on the biosensor surface within a microwell plate such that a surface contains one or more distinct locations, each with a different cell or with a different amount of cells. For example, an array can comprise 1, 10, 100, 1,000, 10,000 or 100,000 or greater distinct locations. Thus, each well of a multiwell plate or microarray can have within it an array of one or more distinct locations separate from the other wells of the multiwell plate, which allows multiple different samples to be processed on one multiwell plate. The array or arrays within any one well can be the same or different than the array or arrays found in any other microtiter wells of the same microtiter plate.

Immobilization of a cell to a biosensor surface can be also be affected via binding to, for example, the following functional linkers: a nickel group, an amine group, an aldehyde group, an acid group, an alkane group, an alkene group, an alkyne group, an aromatic group, an alcohol group, an ether group, a ketone group, an ester group, an amide group, an amino acid group, a nitro group, a nitrile group, a carbohydrate group, a thiol group, an organic phosphate group, a lipid group, a phospholipid group or a steroid group. Furthermore, a cell can be immobilized on the surface of a biosensor via physical adsorption, chemical binding, electrochemical binding, electrostatic binding, hydrophobic binding or hydrophilic binding, and immunocapture methods.

In one embodiment of the invention a biosensor can be coated with a linker such as, e.g., a nickel group, an amine group, an aldehyde group, an acid group, an alkane group, an alkene group, an alkyne group, an aromatic group, an alcohol group, an ether group, a ketone group, an ester group, an amide group, an amino acid group, a nitro group, a nitrile group, a carbohydrate group, a thiol group, an organic phosphate group, a lipid group, a phospholipid group or a steroid group. For example, an amine surface can be used to attach several types of linker molecules while an aldehyde surface can be used to bind proteins directly, without an additional linker A nickel surface can be used to bind molecules that have an incorporated histidine ("his") tag. Detection of "his-tagged" molecules with a nickel-activated surface is well known in the art (Whitesides, *Anal. Chem.* 68, 490, (1996)).

Linkers and specific binding substances can be immobilized on the surface of a biosensor such that each well has the same linkers and/or specific binding substances immobilized therein. Alternatively, each well can contain a different combination of linkers and/or specific binding substances.

A cell can specifically or non-specifically bind to a linker or specific binding substance immobilized on the surface of a biosensor. Alternatively, the surface of the biosensor can have no linker or specific binding substance and a cell can bind to the biosensor surface non-specifically.

Immobilization of one or more specific binding substances or linker onto a biosensor is performed so that a specific binding substance or linker will not be washed away by rinsing procedures, and so that its binding to cells in a test sample is unimpeded by the biosensor surface. Several different types of surface chemistry strategies have been implemented for covalent attachment of specific binding substances to, for example, glass for use in various types of microarrays and biosensors. These same methods can be readily adapted to a biosensor of the invention. Surface preparation of a biosensor so that it contains the correct functional groups for binding one or more specific binding substances is an integral part of the biosensor manufacturing process.

One or more specific cells can be attached to a biosensor surface by physical adsorption (i.e., without the use of chemical linkers) or by chemical binding (i.e., with the use of chemical linkers) as well as electrochemical binding, electrostatic binding, hydrophobic binding and hydrophilic binding. Chemical binding can generate stronger attachment of specific binding substances on a biosensor surface and provide defined orientation and conformation of the surface-bound molecules.

Immobilization of specific binding substances to plastic, epoxy, or high refractive index material can be performed essentially as described for immobilization to glass. However, the acid wash step can be eliminated where such a treatment would damage the material to which the specific binding substances are immobilized.

Methods of Using Biosensors
A. Changes in Cell Growth Patterns

It has been estimated that at least 8-24 hours of laboratory time and the use of a secondary dye are required to quantify total cell movement or cell changes in response to biological entities, such as a protein, peptide or small molecule. See, Reckless & Grainger. 1999. *Biochem. J.* 340: 803-811, Taguchi et al. 1998. *J. Exp. Med.* 187(12): 1927-1940, Jackson et al. 1999. *J. Pharm. & Exper. Therapeutics.* 288(1): 286-294 and Yarrow et al., 2004 *BMC Biotechnol.* 4(21):1-9; see also, U.S. Patent Appl. 2003/0068657, U.S. Patent Appl. 2003/0108954, U.S. Patent Appl. 2004/0091397, U.S. Patent Appl. 2005/0221271, U.S. Patent Appl. 2005/0074825, U.S. Patent Appl. 2005/0058639, U.S. Pat. No. 7,018,838, U.S. Pat. No. 6,982,171, and U.S. Pat. No. 5,601,997. The required amount of time for these types of assays can be reduced to a maximum of 3 hours using methods and compositions of the invention. Additionally, no dyes or detection labels are necessary.

With embodiments of the instant invention cell motility or lack thereof can be detected as it occurs, thus circumventing the need to incorporate radiometric, colorimetric, fluorescent labels or microscopy for evaluation. A colorimetric resonant reflectance biosensor detects directional cell movement and cell attachment as the cells transverse from an area containing no chemoattractant or protein to an area possessing an entity that induces cell motility. Analysis of cellular movement across a biosensor surface can be expediently monitored in real time, in a label free manner. Several other changes in cell growth patterns can be detected using the methods of this invention, such as change in cell morphology, change in cell adhesion, change in cell migration, change in cell proliferation, change in microtubule structure, change in microfilament structure, granule exocytosis, respiratory burst, cell differentiation, fluctuations in adherence, cytoskeletal rearrangement, cellular differentiation, cell death, and protein secretion. A change in a cell growth pattern includes anything that changes a cell's size, shape, height and/or surface uniformity. For cell movement and changes in cell growth patterns to be detected in real time, the BIND Biosensor™, BIND Reader™, and BIND Scanner™ (e.g., a colorimetric resonant reflectance biosensor system) were designed and corresponding algorithms were created to quantify data. See, e.g., U.S. Pat. No. 6,951,715, U.S. Patent Appl. Publ. 2004/0151626.

Methods of the invention are advantageous because they do not require fixing and/or staining of cells for microscopic or colorimetric/fluorimetric evaluation, they allow for continuous, multiple independent readings of the same population of cells in real time, they are quick, they require minimal reagent usage (both volume and type), and they do not require flowing the cells through a counting device. Additionally, the direction and velocity of cell movement or path can be determined in real time.

Methods of the invention allow for continuous monitoring or multiple independent readings of the same population of cells in real time over many days. Cellular changes can be quantified expediently and objectively over longer periods of time in a normal culturing environment (static with proper media). Methods of the invention can also be used synergistically with fluorescent labels to obtain additional, intracellular data from each cell or cell population.

Cell motility can be monitored by taking a PWV for one location over several time periods. Alternatively, scans of a receptacle holding the cells, e.g., a microtiter plate well, can be done over several time periods. A receptacle refers to one container and not a collection of containers, e.g., a multiwell plate.

One or more cells can be applied to a location, such as a microtiter well on a surface of a colorimetric resonant reflectance optical biosensor. A colorimetric resonant reflectance optical peak wavelength value (PWV) for the location is detected. The one or more cells can be incubated for a period of time (e.g., 1 second, 30 seconds, 1, 2, 5, 10, 20, 30, 45 minutes, 1, 2, 5, 10 or more hours). Prior to the incubation, or after the incubation, or prior to the incubation and after the incubation one or more test reagents can be applied to the one or more cells. The colorimetric resonant reflectance optical PWV for the location can be detected for a second time. If a change in cell growth pattern occurs then the reflected wavelength of light is shifted as compared to a situation where no change occurs. The first PWV can be compared to the second PWV. A change in the PWV can indicate a change in cell growth pattern in the one or more cells. PWVs over several time periods can be determined and compared.

Cell growth pattern changes at a biosensor location can be detected via the PWVs of the biosensor surface or monitored more generally using a microscope, digital camera, conventional camera, or other visualization apparatus, magnifying or non-magnifying, that utilizes lens-based optics or electronics-based charge coupled device (CCD) technology.

Preferably, the resolution of the lens of the scanner determining the PWV has an about 2, 4, 5, 6, 7, 8, 9, 10, 11, 12, 13, 14, 15, 16, 17, 18, 19, or 20 micrometer pixel size. Previous scanners had a pixel size of greater than about 20 micrometers. Assays of the invention can be completed in less than 1, 2, 3, 4, 5, 6, 7, or 8 hours. That is, cell changes in response to, for example, and added reagent can be determined in a time efficient manner.

B. Antibody Screening

Another embodiment of the invention provides a method for earlier detection of antibodies that are binding to native targets, e.g., cell surface proteins, in complex mixtures of antibodies and at very low concentrations of antibodies. Low amounts of an antibody on a biosensor surface can be detected by the specific capture of natively folded protein target or cells producing the naturally folded protein target. Another embodiment of the invention provides a method for the detection of low amounts of an antibody in complex mixtures and at very low concentrations.

"Specifically binds" or "specific for" refers to a binding reaction that is determinative of the presence of an antigen in a heterogeneous population of antigens. Antibodies specifically bind to a particular antigen at least two times greater than to the background and more typically more than 10 to 100 times the background. Antibody affinity is the strength of reaction between a single epitope and a single combining site on an antibody.

One embodiment of the invention provides a method of screening antibodies, including those produced by a mixture of different hybridoma cells (including, e.g., hybrid myeloma cells). The different hybridoma cells each produce a different antibody. There can be 2, 100, 1,000, 10,000, 100,000, or more different hybridoma cells in one cell culture. The supernatant from this mixed culture is used to screen for antibodies that specifically bind a protein. The antibodies are immobilized to a colorimetric resonant reflectance biosensor. There can be 2, 100, 1,000, 10,000, 100,000, or more different antibodies immobilized to the biosensor.

An initial peak wavelength can be determined for the biosensor before any molecules are added to its surface as a control. The antibodies are added to a receptacle such as microtiter well, wherein the receptacle has a colorimetric resonant reflectance biosensor as a surface, such as a bottom surface. The antibodies are immobilized to the surface of the biosensor using methods know in the art. For example, protein A can be used to capture IgG via specific interaction with the Fc region of the antibody. Additionally, a rabbit anti-mouse Fc antibody can capture a mouse IgG via specific interaction with the Fc region of the antibody. A peak wavelength value can be determined for the receptacle after the addition of the antibodies. One or more proteins or other biologics, such as natively folded proteins or cells can be added to the receptacle. The receptacle can be washed to remove any non-bound proteins ore other biologics. Another peak wavelength value is determined. The peak wavelength values can be compared. If the peak wavelength value taken after the addition of the proteins or other biologics is higher than the peak wavelength value taken prior to the addition of the proteins or other biologics then one or more antibodies in the receptacle have specifically bound the one or more proteins or other biologics.

The total antibody concentration in the receptacle can be greater than about 0.25, 0.5, 1.0, 10, 50 ug/ml, 1, 2, 3, 4, 5 or more mg/ml. The one or more antibodies in the receptacle, which specifically bind the one or more natively folded proteins, can be present at a concentration of less than about 500, 250, 100, 10, 5, 0.5, 0.1 or less ng/ml. That is, one specific type of antibody, e.g., the antibody a researcher is searching for in a mix of many different types of antibodies can be present at these low concentrations.

The one or more proteins added to the receptacle can be a natively folded protein, such as a cell surface protein. In another embodiment of the invention, one or more whole cells can be added to the receptacle.

A cell, protein, or other biologic can be pre-treated with one or more antibodies prior to the cell, protein, or other biologic being added to the receptacle. The pre-treatment antibodies bind to portions of the protein, cell, or other biologic that are not desired epitopes for the selected test antibody prior to the addition of the proteins, cells, or other biologic to the biosensor surface. The pre-treated proteins or cells or other biologic then are prevented from further interaction with antibodies binding to the undesired epitopes.

Antibody binding at a biosensor location can be detected via the peak wavelength values of the colorimetric resonant reflectance optical biosensor surface or monitored more generally using a microscope, digital camera, conventional camera, or other visualization apparatus, magnifying or non-magnifying, that utilizes lens-based optics or electronics-based charge coupled device (CCD) technology.

Preferably, the resolution of the lens of the scanner determining the PWV has an about 2, 4, 5, 6, 7, 8, 9, 10, 11, 12, 13, 14, 15, 16, 17, 18, 19, or 20 micrometer pixel size. Assays of the invention can be completed in less than 1, 2, 3, 4, 5, 6, 7, or 8 hours. That is, an antibody can be identified from a mix of antibodies that specifically binds to a, e.g., natively folded protein or cell target in a time efficient manner.

C. Cell Based Competition Assays

Methods of the invention can detect cell-antibody or antigen-antibody interactions regardless of media complexity and wherein small amounts or concentrations of cells, antigens and/or antibodies are present. Cells can be captured on colorimetric resonant reflectance biosensors via, e.g., an antibody specific for the cells. About 500, 1,000, 2,000, 2,500, 3,000, 4,000, 5,000 or 10,000 cells can be detected in, e.g., a microtiter well. About 100, 200, 300, 400, 500 pg/mL or 20, 30, 40, 50, 60, 70, 80, 90, 100, or 500 ng/ml of antibody can be used to detect cell interactions in a label-free manner, even in low concentrations of cells (e.g., 1,000, 2,000, 2,500, 3,000, 4,000, 5,000 or 10,000 cells in, e.g., a microtiter well). The detection can be done in complex media such as complete media, HAT media, hybridoma media, human plasma, or serum.

Cell competition assays can be performed using methods described herein even where the cells are present in a complex, non-specific background. For example, cells that are pre-treated with an antigen or antibody or are present in a complex background (such as cell culture media, HAT media, plasma, serum, or hybridoma culture media) can be added to a biosensor that has one or more types of antibodies immobilized to its surface or has no antibodies immobilized to its surface. In one, non-limiting example, an anti-mouse antibody is immobilized to a biosensor. See, Example 1. Control cells that are not pre-treated, and optionally present in a complex background can also be added to the biosensor. Antibodies specific for CD4 will bind the anti-mouse antibody. The biosensor can then be treated with antibodies specific for CD4 or left untreated. One set of cells having CD4 on their surface can be pre-treated with, e.g., one or more antibodies specific for CD4 and/or one or more CD4 antigens. Another set of cells having CD4 on their surface is not pre-treated with the antibodies or antigens. The pre-treated cells and non-pre-treated cells are added to the biosensor. The peak wavelength value for each cell sample is determined. In this example, both the CD4 antigens and antibodies specific for CD4 disrupt the interaction of the cells with the anti-CD4 antibodies. This is demonstrated by changes in the PWVs between each cell sample. Therefore, methods of the invention can be used to perform label-free cell based competition assays where the cells are present in a complex background.

In another non-limiting example, a first antibody is immobilized to a biosensor and a first PWV is determined. A cell preparation is pre-treated with a molecule (e.g., an antibody, cognate receptor binding protein, small molecule, another molecule, etc.) The pre-treated cell preparation is added to the biosensor and the biosensor is optionally washed. A second PWV is determined. The difference between the first PWV and the second PWV is determined. Cell binding to the first immobilized antibody may be increased, decreased, or remain the same depending upon the interaction of the pre-treatment molecule with the cells. If the pre-treatment molecule is a competitive antibody, then the cell binding will decrease.

D. Antibody Ranking

Methods of the invention can be used to screen and rank antibodies produced by, e.g., hybridomas. The methods require very few cells, antigens, and/or antibodies and can be done very early in the a hybridoma screening procedure. In general, B-cells from an antigen-challenged animal are fused with myeloma tumor cells to produce hybridoma cells. The hybridoma cells are diluted to ensure clonality and grown in, e.g., a 96 well tissue culture plate. The monoclonal antibodies produced by the hybridoma clones are tested for their ability to bind to the antigen by, e.g., an ELISA. After hybridoma cells are confirmed to produce an antibody that binds the selected antigen the hybridoma cells are grown in large quantities (e.g. about 30 liters), which can take months to complete. The antibody is purified to greater than 70, 80, 90% or more purity and then antibody ranking as well as other secondary assays can be performed. Antibody ranking is the process of comparing the affinity of antibodies to a particular antigen.

Methods of the instant invention can screen antibodies for binding to the antigen of interest and can also rank the antibodies at the point were the hybridomas are plated as clones and allowed to grow to a density of only about 3,000, 4,000, 5,000, 7,5000, 10,000, 25,000, 50,000, 75,000, 100,000, 200,000 or less cells/well. Therefore, the methods of the invention save a great deal of time in investigating antibodies. Additionally, the methods of the invention can screen and rank the antibodies when they are present in complex media such as cell culture media, HAT media or hybridoma media. That is, the antibodies can be screened and ranked where the antibody purity is low.

A purified antibody preparation, such as a monoclonal antibody preparation, is an antibody preparation that is substantially free of cells, cellular material, cell culture media, other types of antibodies, lysed cells, cell metabolites, cell debris, or combinations thereof. A purified antibody preparation that is substantially free of cells, cellular material, cell culture media, other types of antibodies, cell metabolites, lysed cells, or cell debris has less than about 40%, 30%, 20%, 10%, 5%, 1% or more of cells, cell culture media, cellular material, other types of antibodies, cell metabolites, lysed cells, or cell debris. Therefore, an antibody preparation is about 60%, 70%, 80%, 90%, 95%, 99% or more pure. A non-purified antibody preparation is only about 1%, 5%, 10%, 20%, 30%, 40% or less pure. A non-purified antibody preparation can include, for example, antibodies in hybridoma cell culture media (with or without the cells), periplasmic extracts, non-specific antibodies, cell metabolites, and lysed cell debris.

Unpurified cells are cells that are present in a complex cell culture media such as bovine serum albumin, complete media, HAT media, or hybridoma media. In one embodiment of the invention unpurified cells are those that are present in the media in which they were grown. Such media would include cell media components, cell metabolites, lysed cell debris and other components. In another embodiment, unpurified cells are cells that are present in a media that includes a significant amount of non-specific antibodies.

Methods of the invention can be used to detect differences in antibody affinity in a label-free manner. In one embodiment various types of antibodies specific for a protein, e.g., CD4, can be immobilized at different sites on a biosensor at varying, predetermined concentrations. Unpurified cells in, e.g., complex cell culture media or cells in a complex media comprising non-specific antibodies can be added to biosensor sites and the PWVs determined. The PWVs can be normalized to the amount of antibody immobilized on the biosensor surface. In this manner cell surface antigens, in this non-limiting example, CD4, can be used to detect differences in antibody affinity in a label-free manner.

In another embodiment, methods of the invention can be used to rank antibodies based on their affinity for their ligand. The higher the affinity of an antibody for an antigen, the higher the ratio of: change in PWV Ag/change in PWV Ab. Advantageously, a colorimetric resonant reflectance biosensor scanner can take a peak wavelength value after every addition or change to a biosensor surface condition. For example, an initial PWV can be taken of the biosensor. An antibody can then be immobilized on the surface of the biosensor. A PWV can be taken again. The PWV of the antibody can be adjusted to subtract the baseline reading of the biosensor with nothing attached to it. This would be the antibody PWV. An antigen can then be added to the biosensor. A PWV can be taken. The biosensor baseline reading and the antibody PWV can be subtracted from this PWV resulting in the antigen PWV. All methods of the invention can be performed so that a wash step or a PWV is taken after each addition of material to the biosensor surface.

Methods of the invention allow for the ranking of IgGs in an unpurified monoclonal antibody preparation, e.g., HAT medium (20% bovine serum) in 3 hrs. If the assay is performed in 384 well plates, the subclass of the antibody can be determined simultaneously with ranking.

In another embodiment a colorimetric resonant reflectance biosensor with immobilized anti-Fc allows for specific capture of mouse IgGs from HAT media. This is useful as the antibodies do not need to be purified in order to relatively rank the antibodies based on their affinity for their ligand. The rank is the units of antigen captured per unit of antibody. The higher the affinity of the antibody for the antigen, the higher the BIND™ Ratio ($\Delta$PWV Ag/$\Delta$PWV Ab).

Additionally, antibodies can be binned by their ability to form sandwich pairs without the additional time and resources needed to label the antibodies. Antibody binning refers to whether two or more antibodies are binding to the same region of an antigen. Antibody binning determines whether two or more antibodies can bind to one antigen at the same time. If so, they are binding to different regions of the antigen. If not, they bind at the same region of an antibody. For example, a capture antibody can be immobilized on a colorimetric resonant reflectance biosensor. The biosensor may be blocked and/or washed. A first type of test antibody is added to the biosensor and allowed to bind to the capture antibody. The biosensor can be washed and/or blocked. A test antigen is added to the biosensor and allowed to bind to the first antibodies. The biosensor can be washed and/or blocked. A second type of test antibody is added to the biosensor and allowed to bind to the antigen. If the first and second antibodies bind to different regions of the antigen, they will form a "sandwich" of the first test antibody, the antigen, and the second test antibody. If the first and second antibodies bind to the same region of the antigen the second antigen will be blocked from binding the antigen. More than two species of antibody can be tested at once, such as mouse IgGs, human IgGs and/or chimeric antibodies.

Therefore, antibodies in complex media, such as HAT media can be ranked relative to their affinity as the units of antigen bound per unit of antibody. By ranking antibodies during the first screen of the hybridoma fusion, a subset of IgGs can be selected for limiting dilution and further assays leading to considerable saving of time and resources. Antibodies can be identified as by subclass at the same time as the rank is determined. No labels or secondary detection reagents are required.

Combination of Colorimetric Resonant Reflectance Biosensor and Evanescent Resonant Biosensor Antibody selection processes are not able to discern specific desired biological activity against the target by antibody binding until late in the process in other complex assay formats. The present invention allows for the capture of cells via the target cell surface protein and new test antibody and subsequent testing for the desired biological activity very early on in the antibody discovery process.

As described above, a test antibody can be immobilized on a biosenor surface via, for example, protein A or a rabbit anti-mouse Fc antibody on the sensor surface. The PWV of the sensor is measured and cells are added to the biosensor surface. A PWV is measured and the PWV's compared. Now the cells are captured and can be tested via fluorescent readout (of which there are many known to persons practiced in the art of cellular assays, for example, Euroscreen Calcium chelation assays for ion channel function activity). In one embodiment of the invention, a colorimetric reflectance resonant biosensor is combined with an evanescent resonant biosensor. U.S. patent application Ser. No. 11/490,556, filed on Jul. 20, 2006, discloses a sensor with a substrate having a periodic surface grating structure wherein the periodic grating structure is constructed in a manner designed for both 1) optical interrogation of the sensor with light in an evanescent resonance (ER) detection mode, and 2) optical interrogation of the sensor with light in a colorimetric resonant reflectance label-free detection mode. Therefore, very low level detection of fluorescence that might occur from an infrequently occurring event such as capture of a single cell by a very low copy number of an antibody such as one might encounter early on in the antibody development process.

Grating-based biosensors that have a periodic grating construction that is optimized and useful for both ER detection, either in a liquid or dry environment, and for label-free detection are useful for one embodiment of the invention. See, e.g., U.S. Ser. No. 11/490,556, filed Jul. 20, 2006, which incorporated herein by reference in its entirety. The term "evanescent resonance (ER) detection" or "evanescent resonance (ER) detection mode" is intended to encompass the detection of fluorescence, phosphorescence, chemi-luminescence, electroluminescence, or other type of luminescence, for example as described in Budach et al., U.S. Pat. No. 6,707,561. Such luminescence could be attributable to native luminescence of the sample material or to a bound substance, e.g., fluorescence label, or quantum dots (luminescent metals). Such bound substance may be bound to the sample being tested, the surface of the biosensor, or both.

One-Dimensional Gratings

Figure 3:
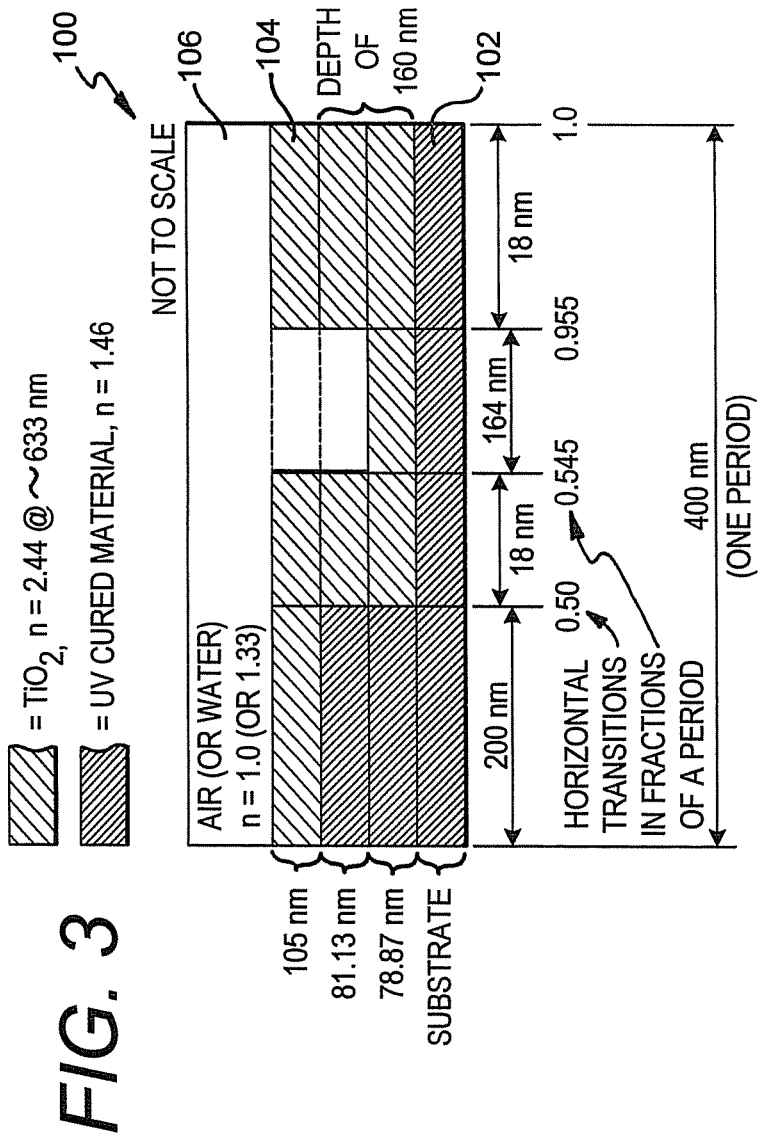
FIG. 3 shows a cross-section of one embodiment of a combined ER and colorimetric resonant reflectance label-free detection biosensor.

FIG. 3 is a schematic cross-sectional illustration of a first embodiment of a one-dimensional sensor having a grating structure 100 that is expected to meet commercial requirements for both ER and colorimetric resonant reflectance label-free applications of a grating-based sensor. FIG. 3 shows one period of a grating structure 100 in one dimension or direction. The dimensions are not to scale in FIG. 3.

The grating 100 of FIG. 3 is superimposed and bonded to a base sheet of clear material such as Polyethylene Terepthalate (PET) or other plastic, glass or other material (not shown).

The grating structure consists of a periodically repeating material 102 which preferably comprises a UV-cured material, e.g., epoxy, applied with the aid of a grating master wafer (not shown) to replicate the grating pattern onto the base sheet of PET material located below the layer "substrate." The UV cured material 102 is applied to a substrate sheet such as PET. Substrate materials can also include polycarbonate or cyclo-olefin polymers such as Zeanor®. Other means of producing the structured layer 102 include thermally stamping directly into a polymer substrate. The middle material 104 represents a sputtered oxide coating with high refractive index (e.g. $TiO_2$ or $Ta_2O_5$). The upper most material 106 represents a medium for a sample, which is normally either a water-based buffer, for label-free detection mode, or air, for ER mode. The structure has the periodicity, layer structure, and horizontal transition points as shown in FIG. 3. The specifics of the design of course may change while still providing good performance for both label-free detection and ER detection.

ER technology heretofore employs a resonance mode induced by incident light with a polarization parallel to the grating, defined here as TE mode or polarization. Label-free detection technology typically employs a resonance mode induced by incident light with polarization perpendicular to the grating, defined here as the TM mode or polarization. This mode produces the narrowest resonance when the sample is suspended in a liquid medium.

In the embodiment of FIG. 3, a grating biosensor design is described which utilizes TM polarization for both label-free detection of a sample suspended in liquid and ER detection in an air (dry) environment. Changing the medium above the grating from water to air results in a change in resonance characteristics from those useful for label-free detection to those useful for ER amplification of dyes responding to 633 nm excitation. The design of FIG. 3 is not specifically optimized to ER detection in a water mode and may not even work acceptably for ER in a water mode. However, many ER detection assays are run in an air environment and so the design of FIG. 3 has much utility for ER detection.

During label-free mode detection, biological molecules adhere to the $TiO_2$ coating and effectively increase the optical thickness of that material. This results in a shift in the peak wavelength value (PWV) of the resonance. A larger PWV shift for a fixed amount of material represents higher detection sensitivity. When comparing grating designs in a computer simulation, the simulation of additional biological material can be modeled by incrementing the thickness of the TiO$_2$ layer rather than adding a hypothetical biological layer. This method has proven effective in other grating design exercises.

To summarize, when dry, the biosensor of this embodiment can amplify fluorescent binding signals according to the technology known as evanescent resonance (ER). When wet, the grating performs as well as a label-free detector according to the technology known as guided mode resonance detection or commercially as BIND™ (trademark of SRU Biosystems, Inc.), available from the applicants' assignee SRU Biosystems, Inc.

Two-Dimensional Gratings

The possibility of a two-dimensional (2-D) grating structure, suitable for both ER and label-free detection, is also contemplated and may be preferred. A two-dimensional grating can look like a waffle (holes), a waffle iron (posts), or a chessboard configuration with alternating high and low regions in two dimensions. Two-dimensional gratings can have different periods in the X and Y directions. These features may have various profiles in the Z direction such as angled or curved sidewalls. Thus, in the case of the waffle pattern, the impressions or wells may have a rectangular rather than a square shape. This added flexibility allows one to tune the resonance positions for both label-free detection and ER detection to occur at different wavelengths. This flexibility offers significant benefit in terms of tuning the ER resonance to different excitation wavelengths while maintaining compatibility with existing label-free detection instrumentation. As an example, the X periodicity can provide a resonance at or near normal incidence with wavelength tuned to excite the CY3 fluorophore (green light) or the CY5 fluorophore (red light), while the Y periodicity can yield a resonance fixed between 820 and 850 nm (in the near infra red).

The specific 2-D embodiments described herein are optimized for combined detection by BIND™ and ER methods in a single device where the sensor contacts water during the BIND™ measurement and air during the ER measurement. Any combination of dry and wet for BIND™ and ER may be similarly optimized (e.g., measure both BIND™ and ER in a wet mode).

A. Holes Embodiment Example

Now, a specific example of a 2D "holes" embodiment of a combined biosensor will be described in conjunction with FIGS. 4A-B. The biosensor is constructed in two dimensions so as to be optimized for both ER and label-free (BIND™) detection using a single device.

FIGS. 4A and 4B provide perspective and cross-sectional views, respectively, of a unit cell for a two-dimensional grating design characterized by periodic holes 210 in a grating structure. The grating design optimizes for water mode BIND™ (label-free) detection and air mode ER detection. The device includes an upper TiO$_2$ layer 104 of 78 nm thickness and a lower substrate 102 layer of UV-cured material having a grating pattern as shown applied to a base substrate sheet.

The structure of FIGS. 4A and 4B is designed in such a way that incident light polarized perpendicular to the X-axis, as shown, produces a BIND™ signal, incident light polarized perpendicular to the Y-axis enables ER measurement. Using this design method, the BIND™ and ER resonant wavelengths (at a particular angle of incidence—preferably near normal incidence) may be chosen independently, and so the respective BIND™ and ER resonant wavelengths may occur at very different values. The combined BIND™/ER structure described in this embodiment is optimized to provide a BIND™ resonance in the near infrared (~800-900 nm) wavelength region, while providing an ER resonance at 632.5 nm for excitation of the Cy5 fluorophore. In this example, the design assumes a water environment over the sensor during BIND™ measurement and an air environment over the sensor during ER measurement. The differing wavelength requirements for ER and BIND™ engender selection of a unit cell with a rectangular "hole" (210). Thus, the unit cell may have differing dimensions in the X and Y directions. For example, the period in the X direction is 550 nm for the BIND™ wavelength, but is 432 nm in the Y direction as required for the lower wavelength ER resonance. The fabrication process dictates that the high refractive index dielectric thickness will be the same in the X and Y directions. For fabrication simplicity, the design also has uniform grating depth. The fabrication process will also result in rounding of the hole corners, however the principal function of the design remains unchanged. One skilled in the art will appreciate that when a computer is used to generate and test a design such as shown in FIGS. 4A and 4B, the designer can change the specific dimensions of the unit cell, grating depth, and coating layers and run simulations of field intensity, peak wavelength, reflectance as a function of theta, and other tests and may select other dimensions while still achieving acceptable results. Thus, the example of FIGS. 4A and 4B is meant to be an illustrative embodiment and not limiting in scope.

B. Posts Embodiment Example

A 2-dimensional grating structure using a repeating unit cell characterized by a post will now be described with reference to FIGS. 5A-B.

FIGS. 5A and 5B are perspective and cross-sectional views, respectively, of a unit cell of 2-dimensional grating design characterized by periodic posts 220 formed in the sensor surface. Each unit cell has one post 220. The posts 220 are raised projections in a substrate material 102 (e.g., UV cured polymer) which is applied to a base sheet (not shown). A high index of refraction (e.g., TiO$_2$) coating is applied to the projections and substrate as shown in FIGS. 5A-B. The structure is optimized for BIND™ (label-free) detection in a water environment using light polarized in the X direction and optimized for ER detection in an air mode, using light polarized in the Y direction.

The design of FIG. 5A-B was studied by RCWA computer simulation. While the previous structure unit cell of FIG. 4 contained a "hole" region surrounded by regions at a higher plane in the z-direction, the grating structure of FIG. 5 contains a central "post" region, surrounded by regions at a lower plane in the z-direction. As before, the design of FIG. 5 represents a BIND™/ER combined structure that is optimized to provide a BIND™ resonance in the near infrared (~800-900 nm) wavelength region, while providing an ER at 632 nm for excitation of the Cy5 fluorophore. In this example, the design again assumes a water environment over the sensor during BIND™ measurement and an air environment over the sensor during ER measurement. These differing wavelength requirements for ER and BIND™, engender selection of a rectangular "post" unit cell. Thus, the unit cell may have differing dimensions in the X and Y directions. For example, the period in the X direction is 530 nm for the BIND™ wavelength, but is 414 nm in the Y direction as required for the lower wavelength ER resonance. The fabrication process again dictates that the high refractive index dielectric thickness will be the same in the X and Y directions. For fabrication simplicity, the design also has uniform grating depth. The fabrication process will also result in rounding of the post corners, however the principal function of the design remains unchanged. The example of FIG. 5 is meant as an illustrative example not limiting in scope. The specific dimensions can of course vary.

C. Two-Level, 2-D Gratings

Figure 6A:
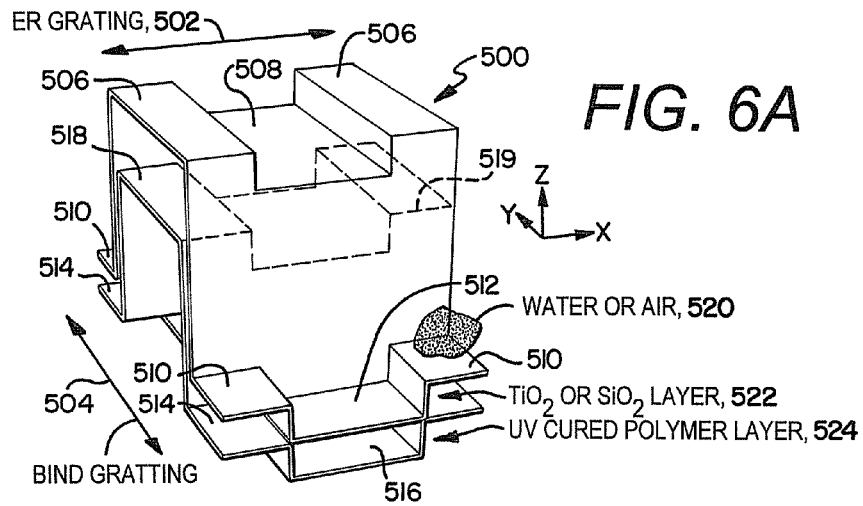
FIGS. 6A-C are three views of a unit cell showing a two-level, two-dimensional grating structure for yet another embodiment of a combined ER and label-free sensor.
Figure 6B:
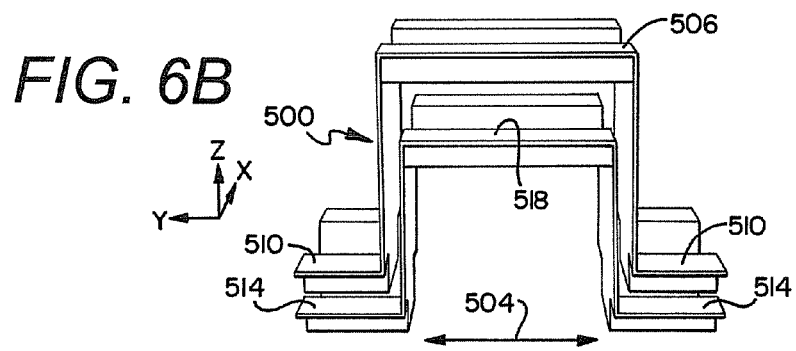
Figure 6C:
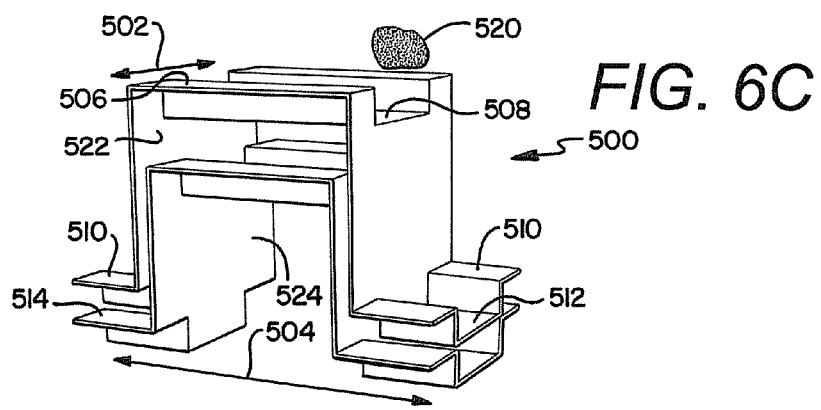

FIGS. 6A-C are three perspective views of yet another embodiment of a unit cell 500 for a biosensor grating structure constructed and designed for a combined ER and label-free (BIND™) detection. In order to appreciate some of the features of this structure, it will be useful to recapitulate on the design aspects pertinent to evanescent resonance (ER) and label-free (BIND™) sensors. Such sensors differ in three basic design aspects, namely: resonance wavelength, resonance width, and grating depth.

Resonance Wavelength

The ER sensor prefers resonance to occur in within a few (~+/−2) nm of the excitation wavelength. Given that the excitation light generally comes from a laser and has very narrow bandwidth, this requirement places high specificity on the wavelength location of the ER resonance. The BIND™ mode of operation does not have this limitation and may benefit from a resonance at another wavelength e.g. outside ambient lighting wavelength range or to separate the BIND™ signal spectrally from the ER excitation source thereby eliminating potential overlapping detection conflicts.

Resonance Width

The ER sensor must have a resonance wide enough for it to overlap the excitation wavelength in the presence of variables such as biological coating thickness and illumination numerical aperture. In practice, the ER resonance should not have a full width at half maximum (FWHM) less than about 5 nm, and more preferably between 10 and 15 nm. On the other hand, BIND™ sensitivity increases approximately as 1/sqrt (FWHM) because peak location uncertainty decreases as the peak width narrows.

Grating Depth

BIND™ sensors give greater resonance wavelength shift when more biological material adheres to the grating. A deeper grating offers more surface area for binding biological material. The ER effect does not necessarily improve and may degrade as the ER grating depth increases.

The 2-D designs described previously have uniform grating depth (e.g. in the post examples the height of the posts, or in the holes example the depth of the holes). Selecting a single grating depth may involve a compromise between BIND™ and ER performance both in terms of peak width and surface area, i.e. BIND™ PWV shift.

The design of the biosensor of FIG. 6A-C is a two-level, two-dimensional design. This design maintains a narrow TM BIND™ resonance and high BIND™ shift performance, while simultaneous providing a wider TE ER resonance. Similar to previously described two-dimensional designs, the BIND™ and ER gratings can have different periods and hence independently determined resonance wavelengths.

This "two level" "comBIND" design of FIG. 6A-C comprises a multitude of repeating unit cells 500, each of which superimposes a relatively shallow ER grating 502 extending in the X direction on a relatively deep BIND™ grating 504, extending in the Y direction. FIGS. 6A-6C depict one "unit cell" 500 for this design, which, when replicated in the XY plane forms the complete grating.

The unit cell 500 consists of a UV-cured polymer layer 524, which is applied using a master grating wafer to a base substrate sheet such as PET film (not shown). The polymer layer 524 has the structure of the BIND™ grating 504, namely alternating low and high regions extending in the Y direction. In the X direction, the grating also has alternating low and high regions, although the relative height of the high region compared to the low regions of the UV-cured polymer layer 524 in the X direction is much less than in the Y direction.

A TiO$_2$ (or alternatively SiO$_2$ or Ta$_2$O$_5$) layer 522 is deposited over the UV-cured polymer layer. This layer has uniform thickness in the illustrated embodiment. The layer 522 includes upper repeating surface 506, 508, 510, and 512, and lower repeating surface 514, 516, 518 and 519. The lower surfaces 514, 516, 518 and 519 are positioned over the top surface of the UV-cured polymer layer. An air or water sample medium 520 is placed in contact with the upper surfaces 506, 508, 510, 512 of the TiO$_2$ or SiO$_2$ layer 522.

As will be appreciated from inspection of FIGS. 6A-C, the "two-layer 2-D" grating structure includes a relatively deep BIND™ grating 504 in the Y dimension, characterized by upper and lower grating surfaces 506/508 and 510/512, respectively. The BIND™ aspect of the unit cell thus permits adding or more sample material and allows more material to adhere to the grating, permitting a greater resonance shift. The deeper grating in the BIND™ (Y direction) offers more surface area for binding biological material.

The ER grating 502 extending in the X direction, conversely, consists of a relatively shallow grating pattern with high regions 506 and low regions 508 (and also high region 510 and low region 512). In addition to providing good BIND™ detection capability, the grating is expected to simultaneously provide a wider TE ER resonance with optimal width.

An apparent advantage of the design of FIGS. 6A-C is that the ER and BIND™ structures should operate independently. Hence, structural dimensions optimized for either ER detection or BIND™ detection alone should work for the combination of the ER and BIND™ sensor of FIG. 6A-C. While the specific dimensions for a structure having the unit cell of FIG. 6A-C is of course variable, in one representative embodiment the BIND™ grating 504 has a period of between about 260 and about 1500 nm, and the depth of the grating (distance between surfaces 506 and 510) is between 100 nm and about 3000 nm. For the ER grating 502, the period is between about 200 nm and about 1000 nm, and the depth (Z distance between surfaces 506 and 508, and 510 and 512) is between 10 nm and about 300 nm.

Readout Systems for Biosensors Combining Label-Free Detection and Fluorescence Amplification (ER)

With the above description of combined ER and label-free biosensors in mind, this document will now describe an embodiment of a readout and detection system useful for interrogating the sensor and acquiring both label-free and ER data from a single binding site on the detector.

Figure 7:
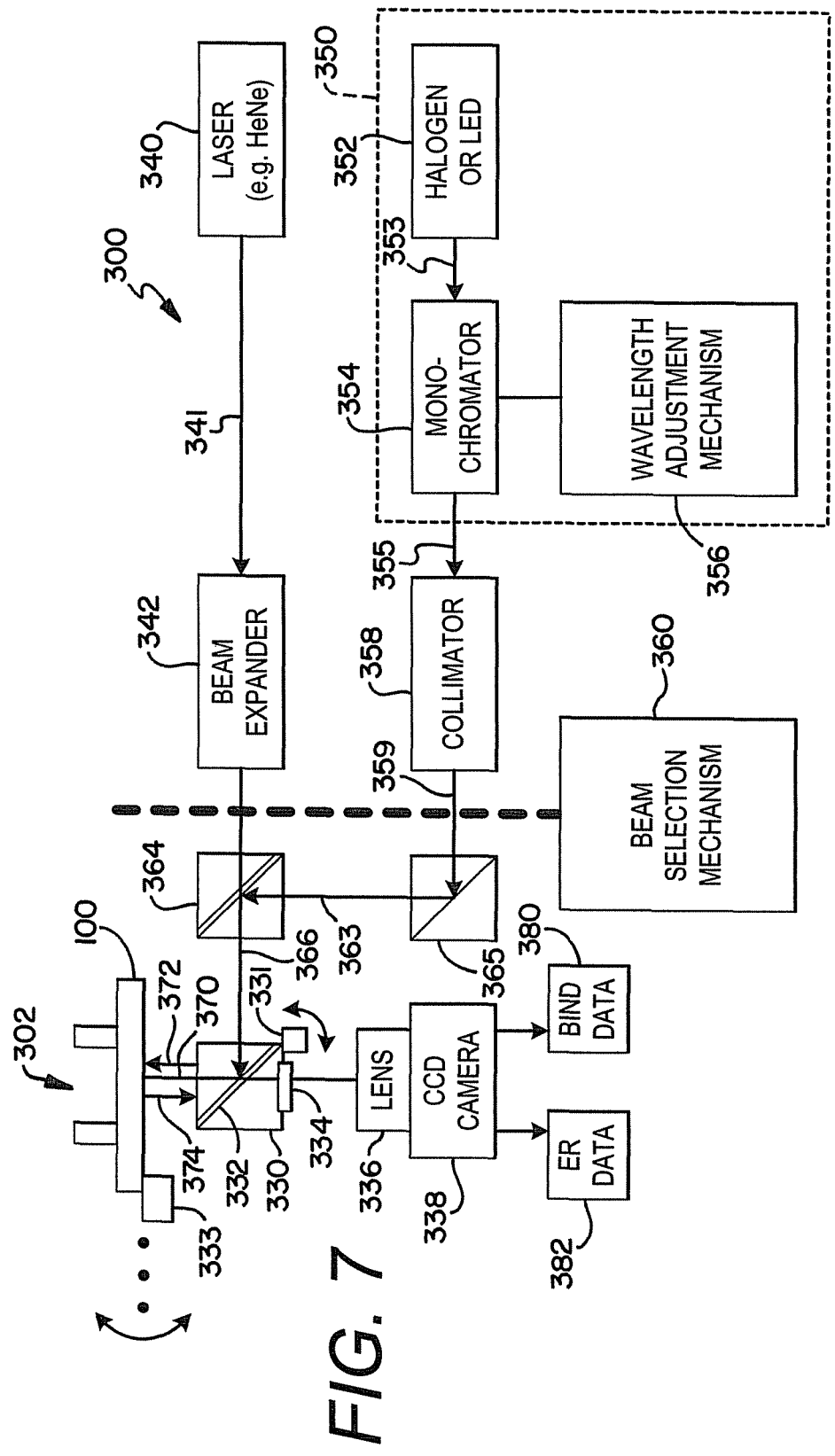
FIG. 7 is a schematic drawing of an imaging readout system for a combined ER and label-free grating-based sensor.
Figure 8A:
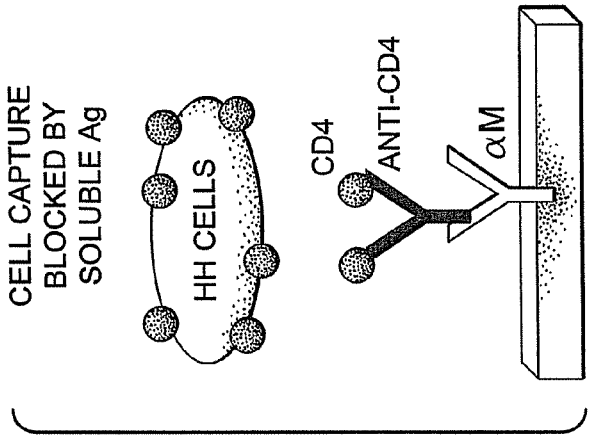
Figure 8B:
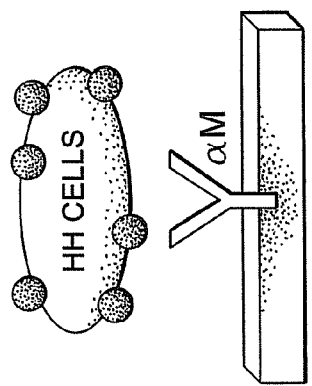
Figure 8C:
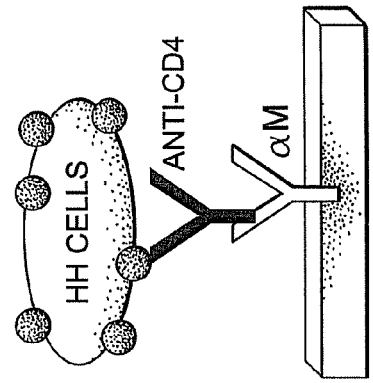
Figure 8D:
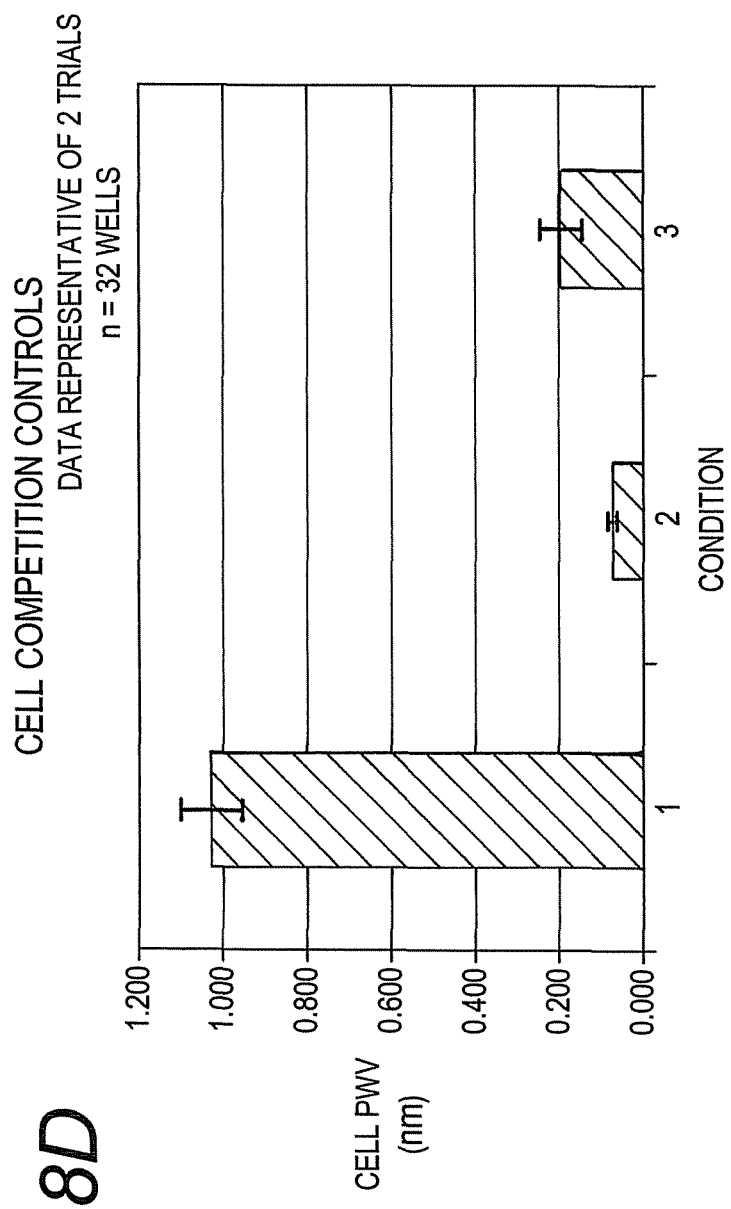
Figure 8H:
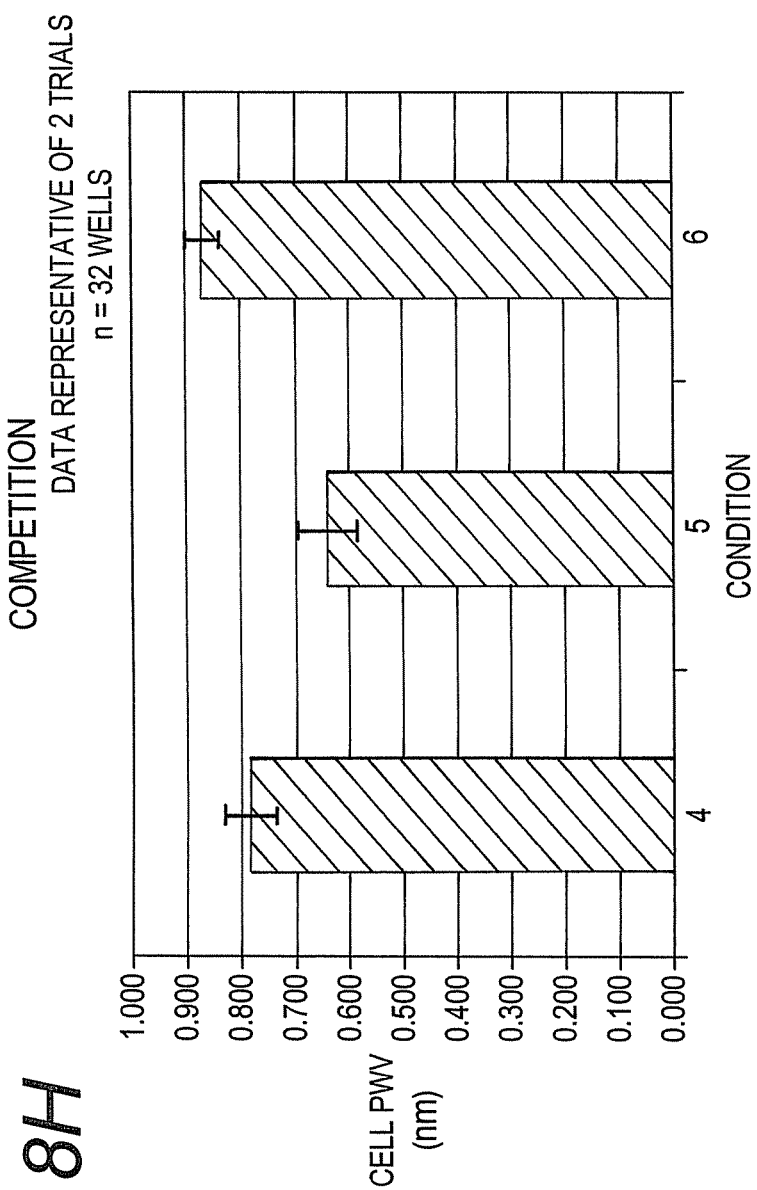

An embodiment of a readout and detection system 300 is shown schematically in FIG. 7. The system 300 of FIG. 7 is an imaging readout system. The biosensor 100 is designed to exhibit both a sharp resonant peak, in the optical spectrum, for label-free detection and a high electromagnetic field in the evanescent region of the biosensor for significant enhancement of fluorescence signal. The readout system reads out both of these effects, taking advantage of these biosensor properties. This disclosure provides a novel imaging readout system with the capability to measure either or both signals from the biosensor.

The biosensor 100, referred to herein as a "comBIND sensor" herein, is interrogated optically from the bottom side of the sensor. On the topside of the biosensor 100, the biosensor may be immersed in water or another liquid, or it may be exposed to air. Any molecular or cellular binding interaction, which the biosensor is designed to detect, takes place on the topside of the biosensor 100. The biosensor 100 may be part of a larger assay device that includes liquid containing vessels, such as for example a microwell plate having e.g., 8 columns of wells, each row containing 12 wells. The biosensor may also be a component of a microarray slide. In the illustration of FIG. 7, a single well (detection site) 302 is shown in cross-section, it being understood that dozens, hundreds or even thousands of such detection sites may be present.

The imaging readout and detection system 300 includes an ER light source 340 in the form of a laser (e.g., HeNe laser), a broader spectrum BIND™ light source 350 including as a halogen white light source or a LED 352, and a CCD camera system 338 serving as a common detector to capture both ER and label-free data in successive images. The system 300 includes an optical beam combining subsystem that includes dichroic mirrors 364 and 330 which serves to combine and direct incident light 372 from the light sources 340 and 352 onto the biosensor. The dichroic mirror 330 collects signal light for detection and directs it to a lens 336 where it is imaged by the CCD camera 338.

The light beam 370 present below the biosensor 100 consists of illumination light 372 and reflected light 374. The reflected light 374 includes direct reflection and fluorescent emission if there is fluorescent material present on the biosensor.

Signal detected by the CCD camera 338 through a lens system 336 is processed electronically or by computer algorithm to become BIND™ (label-free) data 380 or ER data 382. Such data may be stored, displayed, and analyzed on an analytical instrument such as a computer or workstation for the instrumentation shown in FIG. 7 (not shown, but having access to data 382 and 380) by the user of the readout system 300. Furthermore, the combination of the BIND™ data 380 and the ER data 382 allows the user to gain information on binding interactions or cell interactions that is unique to the novel biosensor 100.

In the illustrated design, the optical components 340, 350 and 330 are designed to produce a single beam 372 of incident radiation and the biosensor is moved in X and Y directions to thereby sequentially obtain data from all the wells 302 or binding sites on the biosensor 100 surface. Such motion may be produced by placing the biosensor 100 on an X-Y motion stage (not shown), of which persons skilled in the art are familiar. When a given well or binding site 302 is in position such that the well 302 is in registry with the beam 372, in one embodiment the light sources 340 and 350 are operated in succession (or selectively allowed to direct radiation onto the biosensor) and first and second images are captured by the CCD camera 338, one an ER image and the other a BIND™ image. The successive collection of CCD images could be facilitated by use of the beam selection mechanism 360 (such as a shutter), which selectively allows light from either the source 340 or the source 350 to pass to the dichroic mirror 330 and be reflected onto the biosensor. Beam selection can also be done electronically, such as by electronically controlling the on and off times of the light sources 340 and 350. Alternatively, both light sources could be activated at the same time and the selection mechanism 360 operated to pass both beams so that the incident beam 372 contains light from both sources. In this situation, the CCD camera 338 would capture a single image containing both ER and BIND™ information. Image processing techniques would then be applied to the resultant image from the CCD camera 338 to extract the BIND™ and ER components of the composite image.

The ER light source 340 may be a laser, such as a helium-neon (HeNe) laser. The laser beam 341 further goes through a beam-conditioning device 342 such as a beam expander. The beam expander 342 expands a small diameter laser beam into a large diameter laser beam. The output beam 343 is collimated and linearly polarized. The biosensor produces the ER effect in response to incident light at a specific polarization. Polarization may be achieved by using a laser designed for producing a linearly polarized output laser beam.

The BIND™ (label-free) light source 350 may consist of a halogen or LED light source 352, and a monochromator 354 with a wavelength adjustment mechanism 356. The light beam 353 emitted by the light source 352 is broadband in nature, while the light beam 355 at the exit port of the monochromator 354 is monochromatic.

The output light beam 355 from the monochromator 354 is conditioned by a beam conditioning device 358, which may be a collimator. A mirror 365 directs the light beam 349 from the output of the conditioning device 358 to the dichroic mirror 364. The combined light from the light sources 340 and 350 is shown at 366 where it is directed to the beam splitting and combining assembly 330 which then directs it to the bottom surface of the biosensor 100.

The BIND™ light source 350 may also consist of a tunable laser. In that case, the beam-conditioning device 358 is a beam expander. Note also that a tunable laser or flash lamp could serve as a single illumination source for both BIND™ and ER measurements.

In addition, since polarized light facilitates detection of a BIND™ signal, there may be a polarizer within the light source 352 so that the light 363 is linearly polarized. Alternatively, the light-directing element 365 may be a polarizing beam splitter to transform a randomly polarized light 359 into a linearly polarized light 363.

For detection of the laser excited fluorescence signal, the beam splitting and combining assembly 330 incorporates a set of optical filters 332 and 334. Filter 332 is a dichroic filter that reflects the laser light while transmitting fluoresced light from the sample. Filter 332 also functions as a beamsplitter in the BIND™ wavelength range, which is 830 nm to 900 nm in one preferred design. Filter 334 only allows transmission of light within two wavelength ranges: laser excited fluorescence and the BIND™ wavelength range. An imaging lens 336 may be used to collect the fluorescence light at the biosensor surface and focus it on the focal plane of the CCD camera 338.

The design of FIG. 7 also includes rotation apparatus to rotate the biosensor relative to the incident beam 372 for purposes of ER detection. In one possible embodiment, a rotation device 331 is attached to the beam splitting and combining assembly 330 and rotates the assembly 330 as indicated by the arrows (thereby providing for rotation of the incident beam about angle θ). In an alternative embodiment, rotation device 331 is omitted and instead a rotational device 333 is attached to the XY motion stage which operates to rotate the XY motion stage (and biosensor 100 mounted thereon) relative to the (fixed) incident beam 372, as indicated by the arrows to the left of device 333 in FIG. 7.

Additional lenses, mirrors and optical filters may be incorporated into the readout system to achieve desired performance. Properly designed optical filters may be used to eliminate undesired cross-talk between BIND™ detection and ER detection. In addition, a beam selection mechanism in the form of electronic or mechanical shutters 360 may be used to properly synchronize light illumination and detection of the two channels, so that only one light source illuminates the biosensor at a given time, to eliminate any cross-talk.

A significant advantage of the biosensor readout system described in FIG. 7 is that both BIND™ and ER data may be collectedly simultaneously (or in rapid succession) at the same biosensor location. High-resolution imaging methods are useful for high content bioassays such as cell-based assays or microarrays.

An integrating single point detector may replace the CCD camera 338. In that case, the system produces an image by synchronizing sensor motion, over the location of the incident radiation 372, with the detector output.

Further details on use of a CCD camera to obtain ER data from a biosensor can be found in the technical literature, e.g., an article of Dieter Neuschäfer, Wolfgang Budach, et al., Biosensors & Bioelectronics, Vol. 18 (2003) p. 489-497, the contents of which are incorporated by reference herein.

All patents, patent applications, and other scientific or technical writings referred to anywhere herein are incorporated by reference in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims. In addition, where features or aspects of the invention are described in terms of Markush groups or other grouping of alternatives, those skilled in the art will recognize that the invention is also thereby described in terms of any individual member or subgroup of members of the Markush group or other group.

EXAMPLES

Example 1

Cell Based Competition Assay

Anti-mouse antibody was immobilized on a 384-well BIND™ biosensor. Anti-CD4 was captured on various surfaces with and without cells. 50,000 HH cells were added to each well in the presence of cell media containing 10% FBS with 1% penicillin-streptomycin. These cells were either pre-incubated with or without antibody and/or soluble antigen. The PWV was detected for each well. The total measurement time on a BIND™ Reader was 20 minutes (only 1 minute measurement time per plate is needed; however, the plate was scanned 3 times in this particular example). The total assay time was 4 hours. The results are shown in FIG. 8A-H. Both antibody and soluble antigen disrupt cell interaction with immobilized antibody. Detection of cell based competition is successful in backgrounds such as complete media.

Example 2

Detection Sensitivity in Cell Based Assays

Figure 9:
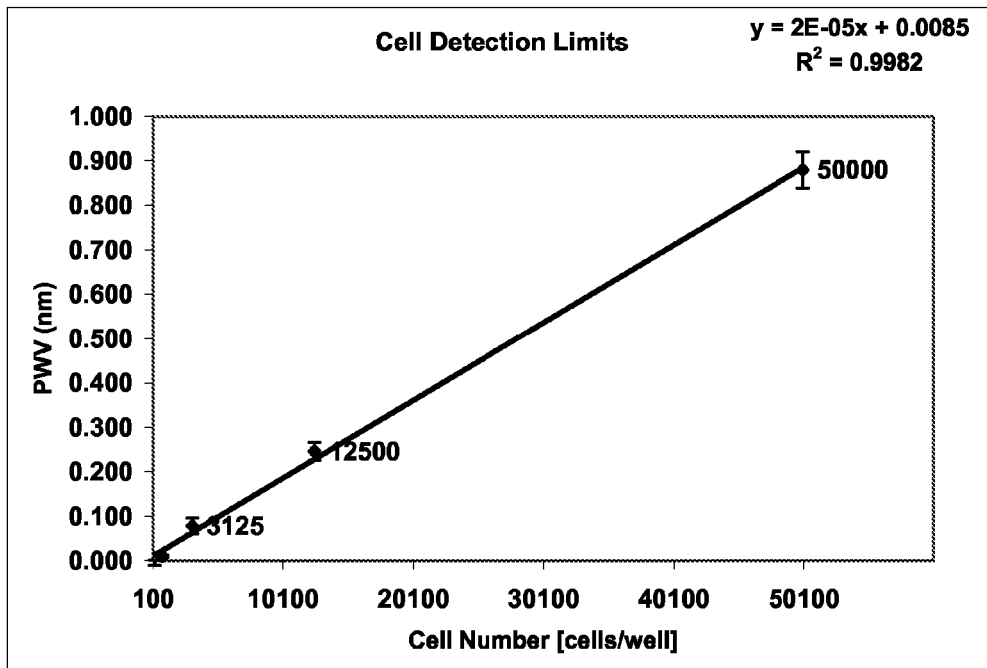
FIG. 9 shows results of a cell based assay.

An anti-mouse antibody was immobilized on a 384-well BIND™ biosensor. Mouse monoclonal anti-CD4 was then added. Various concentrations of HH cells, with endogenous expression of CD4, were captured. Cells were added to each well in the presence of cell media containing 10% FBS with 1% penicillin-streptomycin. PWVs were determined for each well. The total measurement time on a BIND™ Reader was 15 minutes (only 1 minute measurement time per plate is needed, however, the plate was scanned 3 times in this particular example). The total assay time was 3 hours. The results are shown in FIG. 9. As little as 3,125 cells/well can be detected. Detection of natively expressed cell surface antigens is rapid. Capture of cells is successful in various backgrounds such as complete media or hybridoma media.

Figure 10:
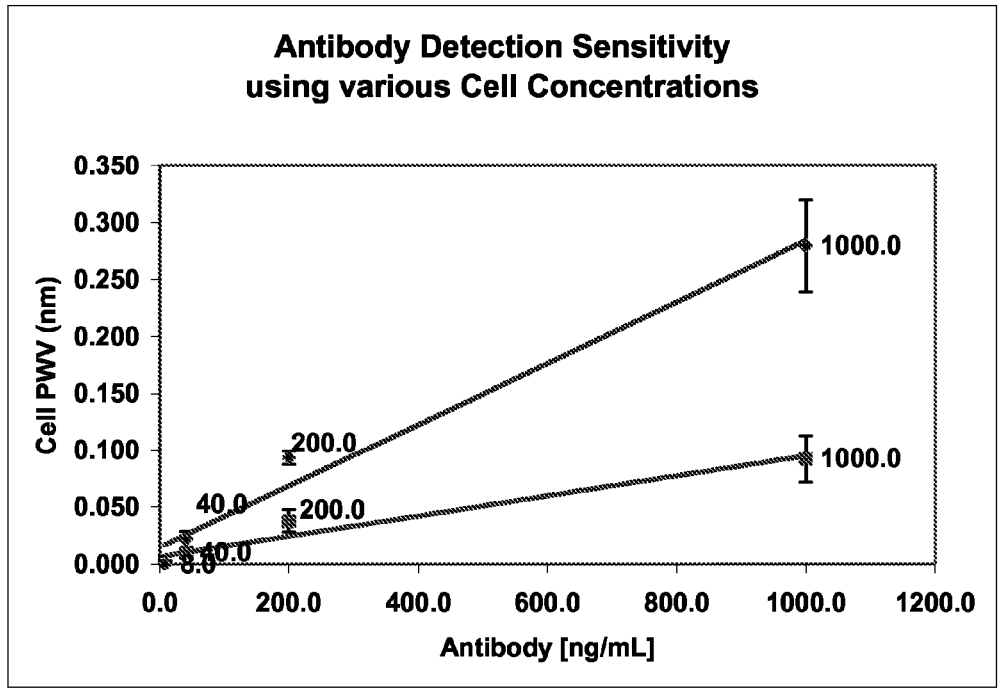
FIG. 10 shows results of a cell based assay.

In another experiment anti-mouse antibody was immobilized on a 384-well BIND™ biosensor. Various concentrations of anti-CD4 were captured. HH cells were added to each well in the presence of cell media containing 10% FBS with 1% penicillin-streptomycin. The total measurement time on the BIND™ Reader was 15 minutes (only 1 minute measurement time per plate is needed, however, the plate was scanned 3 times per protocol step in this particular example) and the total assay time was 3 hours. The results are shown in FIG. 10. In this particular assay, with these cells, as little as 40 ng/mL (0.6 ng/well) of antibody can be used to detect cell interaction in a label-free manner (with Jurkat cells as little as 500 pg/mL of antibody can be used). Low concentrations of cells can be utilized such as 3,000 cells/well. Detection of antigens can be done in various backgrounds such as complete media, human plasma, or serum (data not shown for plasma or serum).

Example 3

Antibody Ranking in Cell Based Assays

Figure 11:
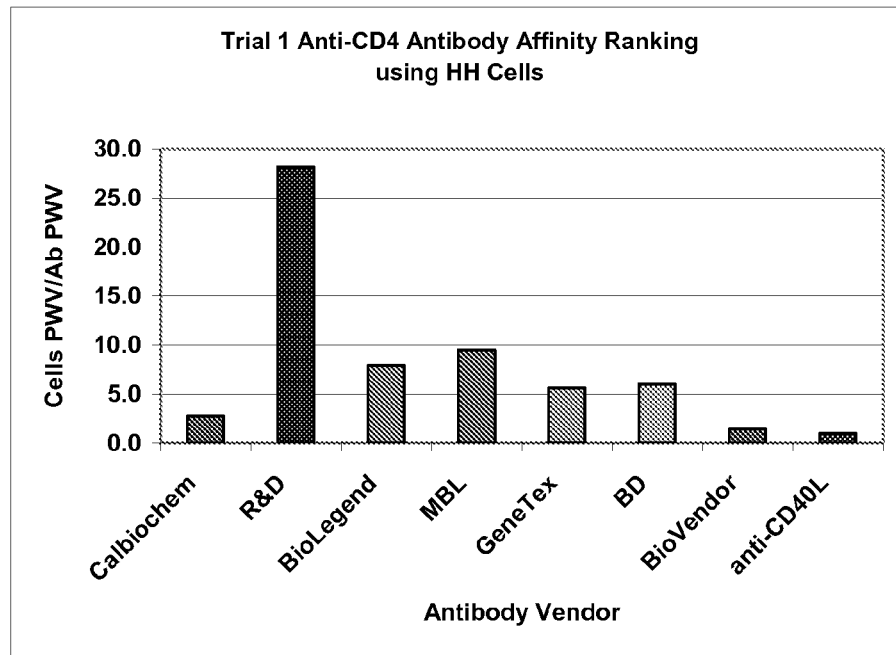
FIGS. 11A-B show the results of a cell based antibody affinity ranking assay.
Figure 11:
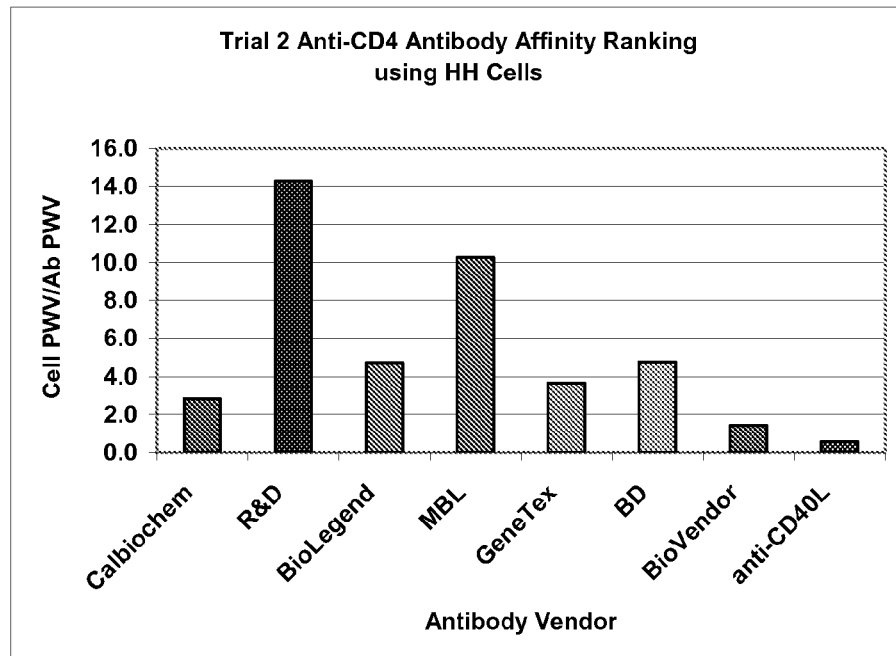

Anti-mouse antibody was immobilized on a 384-well BIND™ biosensor. Various anti-CD4 antibodies at set concentrations were captured on the biosensor surface. 50,000 HH cells were added to each well in the presence of cell media containing 10% FBS with 1% penicillin-streptomycin. The cell PWV signal was normalized to the amount of anti-CD4 antibody immobilized on the BIND™ biosensor surface. The total measurement time on a BIND™ Reader was 15 minutes (only 1 minute measurement time per plate is needed, however, the plate was scanned 3 times in this particular example). Total assay time was 2.5 hours. The results are shown in FIG. 11A-B. Cell surface antigen can be used to detect differences in antibody affinity in a label-free manner.

Example 4

Detection of Cell-Antibody Interactions in Complex Media

Figures 12, 13:
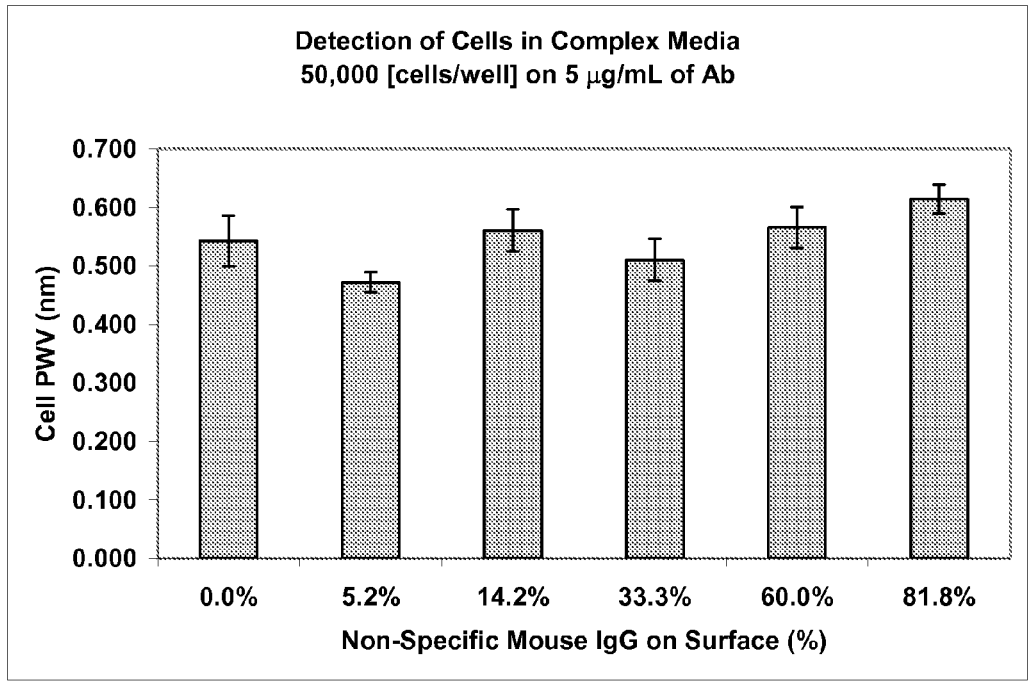
FIG. 12 demonstrates detection of cell-antibody interactions in complex media.
FIG. 13 demonstrates ranking of mouse IgGs in HAT medium.

Anti-mouse antibody was immobilized on a 384-well BIND™ biosensor. Anti-CD4 antibody was captured in the presence of mouse IgG. Using the same plate, 50,000 HH cells were added to each well. The change in PWV was measured. The total measurement time on BIND™ Reader was 20 minutes (only 1 minute measurement time per plate is needed, however, this plate was scanned 3 times in this particular example) and the total assay time was 3.5 hours. The interaction of cell surface antigen with antibody was specifically detected in the presence of non-specific antibody background (mouse IgG). See FIG. 12.

Example 5

Specific Capture of Mouse IgGs

One of the challenges of using hybridoma technologies is the large number of antibodies that bind the antigen (soluble or on cells) in standard assays such as ELISA. In order to move candidates forward in a work flow more information is required. Ranking of IgGs earlier in the process will shorten time lines for identification of lead candidates for preclinical trials. The methods of the invention allows for the ranking of IgGs in HAT medium (20% bovine serum) in 3 hrs. If the assay is performed in 384 well plates, the subclass of the antibody can be determined simultaneously with ranking.

An anti-Fc BIND™ Biosensor allows for specific capture of mouse IgGs from HAT media. This is useful as the antibodies do not need to be purified in order to relatively rank the antibodies based on their affinity for their ligand. The rank is the units of antigen captured per unit of antibody. The higher the affinity of the antibody for the antigen, the higher the BIND™ Ratio ($\Delta$PWV Ag/$\Delta$PWV Ab).

Four anti-mouse antibodies ($\alpha$M-A, B, C, & D) were immobilized directly to a GA1 BIND™ biosensor for thirty minutes then washed 3× with PBST. A baseline read was taken. Mouse, bovine and human IgGs in PBST were incubated with the anti-mouse surface for 1 hour in order to determine specificity of the anti-mouse antibodies. The mass corresponding to the IgG is recorded. The mass is relative to the shift in the wavelength in light [$\Delta$PWV in picometers (pm)] due to mass accumulating on the biosensor. Using EMS software the mouse IgG was baselined to zero. Antigen (soluble or expressed on cells) was added to the wells, then excess antigen was washed away. As in the previous step, the mass corresponding to the amount of antigen binding through the antibody was recorded. The antibodies were ranked using the following equation:

$\Delta$PWV of Antigen/$\Delta$PWV of Antibody

In addition, a titration of mouse IgGs from 1-40 ug/ml was tested for dose dependent binding in HAT medium. The results are shown in Table 1.

TABLE 1

| Capture Antibody | 8 ug/ml Mouse IgG (pm) | 8 ug/ml Bovine IgG (pm) | 4 ug/ml Human IgG (pm) | % Bovine IgG of Mouse IgG | Dose Dependent Binding of Mouse IgG In HAT medium (20% serum) | Captures M-IgG subclasses equally in HAT medium (20% serum) |
|---|---|---|---|---|---|---|
| $\alpha$M-A | 198 | 8 | 2 | 4 | No | No |
| $\alpha$M-B | 126 | 15 | 9 | 12 | No | No |
| $\alpha$M-C | 204 | 2 | 5 | 1 | Yes | No |
| $\alpha$M-D | 138 | 2 | 0 | 1 | Yes | Yes |

The anti-mouse IgG BIND™ Biosensor surface based on capture antibody D is specific for capture of mouse IgGs in a dose dependent manner. HAT medium contains 20% fetal bovine serum. If the capture antibodies bind bovine IgGs as well as mouse IgGs, then the signal recorded during the antibody capture will be a composite of both types of antibody. In addition, if there is more bovine than mouse IgG, then the signal will not be dose dependent. Only capture antibody D performs well in HAT medium (20% serum).

Example 6

Development of Methodology for Ranking Mouse IgGs in HAT Medium

A GA1 BIND™ Biosensor was coated with capture antibody D (CAb$_D$). The anti-mouse BIND™ Biosensor was blocked with HAT medium (20% serum) for thirty minutes then washed 10× with PBST. 25 ul PBST was aliquoted onto the blocked biosensor. Purified mouse IgGs were diluted in serial 2-fold dilutions into HAT medium (20% serum), then 25 ul of mouse-IgG dilutions were added to the wells containing 25 ul of PBST (another 2-fold dilution). After one hour of incubation the biosensor was washed 5× with PBST. The normalized PWV ($\Delta$PWV) in picometers (pm) for the IgG binding was recorded. 50 ul of 4 ug/ml antigen was incubated with the captured mouse IgGs for an hour, then washed 3× with PBST. The $\Delta$PWV (pm) was recorded for the amount of antigen captured by the immobilized mouse antibodies. During the development of the method, multiple concentrations of the antibody were captured to ensure that the rank was independent of the amount of IgG captured on the BIND™ Biosensor.

The theoretical ratio is calculated as follows:

2×Antigen MW/IgG MW=1.2

The empirical ratio is calculated as follows:

$\Delta$PWVAg(pm)/$\Delta$PWVIgG(pm)

The ratio for samples with IgG (pm)>50 and Antigen>30 (BOLD in FIG. 13) was calculated. The average ratios are in BOLD for relative rank in FIG. 13. LEX-1 had an average ratio of 0.56 and a standard deviation of 0.09. LEX-2 had an average ratio of 0.69 and a standard deviation of 0.09. LEX-9 had an average ratio of 0.61 and a standard deviation of 0.05. IgG-1 had an average ratio of 0.13 and a standard deviation of 0.12.

Example 7

Reproducibility of Rank of Mouse IgGs in HAT

Three anti-mouse antibodies ($\alpha$M-D, $\alpha$M-E (anti-subclass-1) and $\alpha$M-F (anti-subclass-2a)) were immobilized directly to two GA1 BIND™ Biosensors (GA1 0048 and GA1 0049) for thirty minutes then washed 3× with PBST. The biosensors were blocked in HAT, then washed 10× with PBST. Mouse IgGs (LEX-1 to 10) were diluted to 20 ug/ml in HAT (25 ul), then diluted 2-fold into PBST (25 ul) on the biosensor. The IgGs were incubated for 1 hour, then washed 5× with PBST. The $\Delta$PWV was recorded. 4 ug/ml of antigen was added to the biosensor for 1 hour then washed 5× with PBST. The $\Delta$PWV was recorded.

The ratio was calculated and sorted based on percentage theoretical ratio.

Empirical Ratio ($\Delta$PWV Ag/$\Delta$PWV IgG)/Theoretical Ratio (2×MW Ag/MW IgG)×100

Theoretical Ratio=(2×90 kDa/150 kDa)=1.2

Figures 14C, 15:
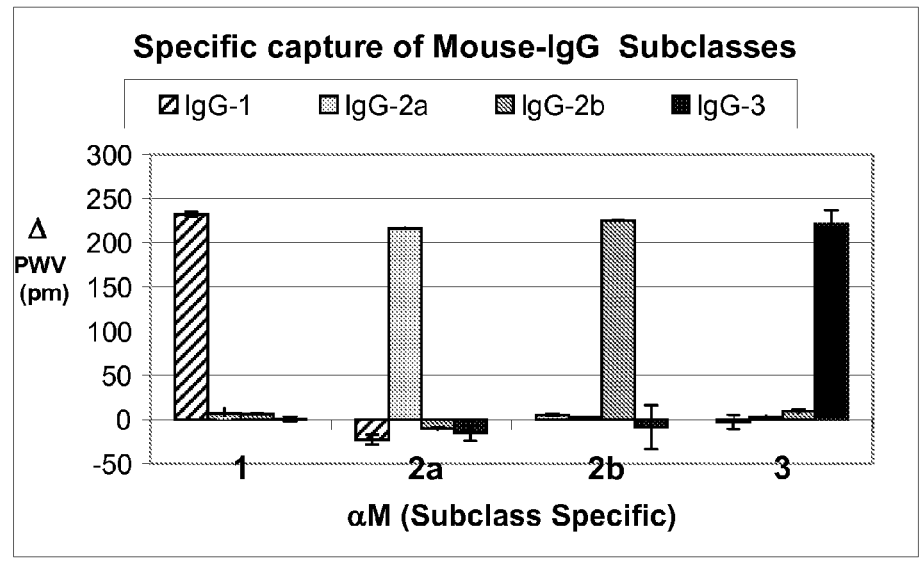

The results are shown in FIGS. 14A-C. The experiments demonstrate the reproducibility of ranking IgGs in HAT is high across different anti-mouse antibodies on two different GA1 BIND™ Biosensors. When the IgGs were sorted based on % Theoretical Ratio (Ratio/1.2×100), they sorted within 4 groups: (1) <5% (Non Binders); (2) 5-20% (uM); (3) 39-48% (10-50 nM); and (4) >49% (≤10 nM).

Example 8

Specificity of Anti-Mouse Subclass Antibodies

Anti-mouse antibodies specific for each subclass were immobilized to a GA1 BIND™ Biosensor. Purified IgGs for each subclass were incubated with each of the anti-mouse capture antibodies. The results are shown in FIG. 15. The anti-mouse subclass specific antibodies are specific enough to determine the subclass and rank the antibodies simultaneously.

Example 9

Detection of Mouse IgGs from Limited Dilution of a Hybridoma Clone

A hybridoma clone from a fusion was thawed and plated at a limiting dilution in HAT medium (20% serum). The cells were allowed to grow for 2 weeks. The plate was inspected for the presence of colony growth (see, FIG. 16 (shading)). αM-D antibody was added to a GA1 BIND™ biosensor and the biosensor was blocked with HAT medium. 25 ul of medium from limited dilution clones was added to the biosensor. The results are shown in FIG. 16. BIND™ selects 14 (BOLD) of 15 clones identified via visual inspection of the colonies (B5 was missed). BIND™ identified 4 additional wells producing antibody (A2, D1, D4, & G4). The cutoff for M-IgG binding was 25 pm as the wells denoted as not containing M-IgG (not Bold) is −5.8±8.2 pm.

Example 10

Comparison of the Rank of IgGs in the Crude and Purified Assays

Once antibodies have been ranked in a primary screen, wherein the antibodies are present in hybridoma medium or as periplasmic extracts, the antibodies can be further characterized with methods of the invention.

FIG. 17 shows that the rank of mouse IgGs determined in HAT medium is equivalent to the rank of the purified antibody in PBS, while FIG. 18 shows the ranking assay for human IgGs as well as F(ab)s.

A capture surface (αM-D) specific for mouse IgGs (LEX-1 to 10) was immobilized on Gluteraldehyde (GA1) BIND™ Biosensors for thirty minutes then washed 3× with PBST. 10 ug/ml of mouse antibodies were incubated with the biosensor for 1 hour, then washed 3× with PBST. The ΔPWV in picometers (pm) for the antibody captured per well was determined. 4 ug/ml of Antigen #1 (90 kDa) was incubated with the antibodies for 1 hour then washed 3× with PBST. The ΔPWV in (pm) was recorded for the bound antigen. The ratio or ΔPWV Ag/ΔPWV Ab was determined.

Another experiment was performed that was similar to that described above, except the capture surfaces (αH-G and αH-H) were specific for human IgGs (LEX-11 to 15) and for soluble F(ab)s, respectively. See FIG. 18. The percentage theoretical ratio equals the empirical ratio (ΔPWV Ag/ΔPWV Ab) divided by the theoretical ratio (number of binding sites× MW Ag/MW Ab) times 100.

The results show that the methods of the invention are useful for relatively ranking antibodies based on their affinity for their ligand. The rank is the units of antigen captured per units of antibody. The higher the affinity of the antibody for the antigen, the higher the BIND™ Ratio (ΔPWV Ag/ΔPWV Ab).

Example 11

Antibody Binning to Find Sandwich Pairs

Figure 19:
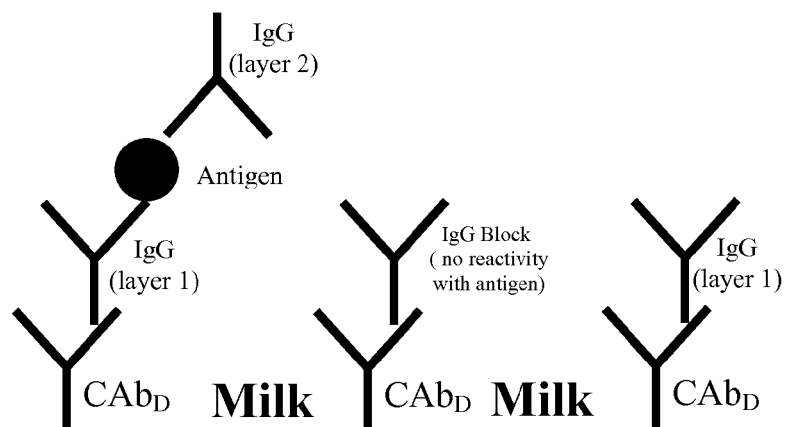
FIG. 19 shows an antibody binning assay to find sandwich pairs

Antibodies were classified by their ability to sandwich pair on an antigen. This provides another useful way to characterize a large number of antibodies to one target. A GA1 BIND™ biosensor was incubated with an anti-human (αH) capture antibody for 30 min., then washed 3×PBST. LEX-20, 21 and 22 are chimeric antibodies (Human-Fc). The biosensor was blocked for 30 min with 1% milk, then washed 10× with PBST. 5.0 ug/ml LEX-20, 21 and 22 were incubated for 1 hr., then washed 3× with PBST. Any remaining anti-human binding sites were blocked with excess human-Fc for 30 min and washed 3× with PBST. 1.5 ug/ml Ag #2 (300 kDa) and 4.0 ug/ml Ag #3 (110 kDa) were incubated with the antibodies for 1 hr, then washed 3× with PBST. 5.0 ug/ml of the 2nd antibody was incubated for 1 hr, then washed 3× with PBST. See FIG. 19. LEX-30 and 31 are mouse antibodies. The results are shown in FIG. 20.

The above experiment was repeated with the following modifications. The GA1 BIND™ biosensor was coated with LEX-30, a mouse-IgG. LEX-30 (129.1+10.2 pm, N=72) was the only antibody captured on the anti-mouse GA1 BIND™ Biosensor. The biosensor surface was blocked with excess Mouse IgG. 1.5 ug/ml of Antigen 2 bound to Lex-30 (87.0+ 8.4 pm, N=44). LEX-30 paired with 11 antibodies of the 19 antibodies tested. See FIG. 21. In FIG. 21 the shaded IgG are >4 fold above the background binding to LEX-30 with antigen versus without antigen. The IgG-1 is 3.5 fold on Antigen versus the PBST control. Multiple BIND™ Biosensors can be run at one time without increasing the assay time significantly as a 96-well plate is read in 30 sec.

Therefore, even after ranking, a large number of antibodies may remain as potential leads. Binning the antibodies by the ability of two antibodies (a sandwich pair) to bind the same antigen at the same time is useful to determine whether the antibodies bind the same region of an antigen.

Example 12

Detection of Growth Factor Induced Cell Morphology Changes

Cell morphological changes on a colorimetric resonant reflectance biosensor can be detected with a scanner having a resolution of 7.6 um. Swiss 3T3 cells were grown on a colorimetric resonant reflectance biosensor. The cells were grown to confluence. The cells were serum starved for 10 hours and then growth factor (PDGF), fetal bovine serum (FBS), or calf bovine serum (CBS) were added to the cells. The PWV decreases when lamellopodia are formed due to PDGF exposure. The PWV increases when stress fibers are formed when FBS or CBS are added to the cells. The results are shown in Table 2. The "reader" reads only a 2 mm diameter in the well, the "scanner" scans the entire well.

TABLE 2

| | Treatment | Mean ΔPWV |
|---|---|---|
| Scanner | 5 ng/ml PDGF | −0.074 |
| | 3 ng/ml PDGF | −0.114 |
| | 1% FBS | 0.325 |
| | 1% CBS | 0.303 |
| Reader | 5 ng/ml PDGF | −0.331 |
| | 3 ng/ml PDGF | −0.153 |
| | 1% FBS | 0.163 |
| | 1% CBS | 0.247 |

We claim:

1. A method of screening about 100 or more different antibodies in one receptacle comprising:
   (a) immobilizing the antibodies to a colorimetric resonant reflectance biosensor, wherein the colorimetric resonant reflectance biosensor comprises an inner surface of the receptacle;
   (b) determining a first peak wavelength value for the receptacle;
   (c) adding one or more natively folded proteins to the receptacle;
   (d) determining a second peak wavelength value for the receptacle;
   (e) comparing the first and second peak wavelength values wherein, if the second peak wavelength value is higher than the first peak wavelength value, then one or more immobilized antibodies in the receptacle have specifically bound the one or more natively folded proteins.

2. The method of claim 1, wherein the total antibody concentration in the receptacle is greater than 2 mg/ml.

3. The method of claim 1, wherein the one or more antibodies in the receptacle that have specifically bound the one or more natively folded proteins are present at a concentration of less than 5 ng/ml.

4. The method of claim 1, wherein the natively folded protein is a cell surface protein.

5. The method of claim 1, wherein the natively folded protein is part of a whole cell that is added to the receptacle.

6. The method of claim 5, wherein the cell is pre-treated with one or more antibodies prior to the cell being added to the receptacle.

7. The method of claim 1, wherein the antibodies are produced by about 100 or more different hybridoma cells.

8. The method of claim 1, wherein the antibodies are produce by about 1,000 or more different hybridoma cells.

9. A method of detecting specific binding of a first antibody to a protein, wherein the antibody is in a mixture of more than 100 different antibodies, wherein the first antibody is in the mixture of antibodies at a concentration of less than about 3 ng/ml, and wherein the concentration of the mixture of antibodies is greater than about 3 ug/ml comprising:
   (a) immobilizing the mixture of antibodies to a colorimetric resonant reflectance biosensor, wherein the colorimetric resonant reflectance biosensor comprises an inner surface of the receptacle;
   (b) determining a first peak wavelength value for the receptacle;
   (c) adding one or more proteins to the receptacle, wherein one or more of the proteins may specifically bind to the first antibody;
   (d) determining a second peak wavelength value for the receptacle;
   (e) comparing the first and second peak wavelength values wherein, if the second peak wavelength value is higher than the first peak wavelength value, then one or more antibodies in the receptacle have specifically bound the one or more of the proteins.

10. A method of detecting specific binding of a first antibody to unpurified cells or unpurified antigen comprising:
    (a) immobilizing the first antibody to a colorimetric resonant reflectance biosensor;
    (b) detecting a first peak wavelength value;
    (c) adding the unpurified cells or unpurified antigen to the colorimetric resonant reflectance biosensor;
    (d) detecting a second peak wavelength value;
    (e) comparing the first and second peak wavelength values, wherein an increase in the second peak wavelength value indicates specific binding of the first antibody to the unpurified cells or unpurified cells.

11. The method of claim 10, wherein a first antigen specific for the first antibody is added to the unpurified cells or unpurified antigen prior to adding the unpurified cells or unpurified antigen to the colorimetric resonant reflectance biosensor, and wherein a lower second peak wavelength value than the second peak wavelength value of claim 10 indicates specific binding of the unpurified cells or unpurified antigen to the first antigen.

12. The method of claim 10, wherein a second antibody having the same specificity as the first antibody is added to the unpurified cells or unpurified antigen prior to adding the unpurified cells or unpurified antigen to the colorimetric resonant reflectance biosensor, and wherein a lower second peak wavelength value than the second peak wavelength value of claim 10 indicates specific binding of the unpurified cells or unpurified antigen to the second antibody.

13. The method of claim 10, wherein the unpurified cells are about 10,000 or fewer cells.

14. The method of claim 10, wherein the concentration of the first antibody is about 3 ng/ml or less.

15. The method of claim 10, wherein the unpurified cells are present in HAT media, hybridoma media, or cell culture media.

16. The method of claim 10, wherein the first antibody, unpurified cells, and unpurified antigen do not comprise detection labels.

* * * * *